(12) United States Patent
Lumauig et al.

(10) Patent No.: US 9,700,443 B2
(45) Date of Patent: Jul. 11, 2017

(54) METHODS FOR ATTACHING A RADIOPAQUE MARKER TO A SCAFFOLD

(71) Applicant: Abbott Cardiovascular Systems Inc., Santa Clara, CA (US)

(72) Inventors: Rommel Lumauig, San Jose, CA (US); Joel Harrington, Redwood City, CA (US); Chad Abunassar, San Francisco, CA (US); David D. Hart, Temecula, CA (US); Cornel I. Ciurea, Murrieta, CA (US); Mark A. Ritchie, Fallbrook, CA (US); Jay A. King, Temecula, CA (US); Jill McCoy, Sunnyvale, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 13 days.

(21) Appl. No.: 14/738,710

(22) Filed: Jun. 12, 2015

(65) Prior Publication Data

US 2016/0361182 A1 Dec. 15, 2016

(51) Int. Cl.
*A61F 2/82* (2013.01)
*A61F 2/915* (2013.01)
(Continued)

(52) U.S. Cl.
CPC .............. *A61F 2/915* (2013.01); *A61F 2/844* (2013.01); *A61F 2/86* (2013.01); *A61F 2/89* (2013.01); *B21J 15/02* (2013.01); *B21J 15/14* (2013.01); *A61F 2002/3008* (2013.01); *A61F 2002/91575* (2013.01); *A61F 2210/0014* (2013.01); *A61F 2220/0033* (2013.01); *A61F 2230/0026* (2013.01); *A61F 2230/0069* (2013.01); *A61F 2240/001* (2013.01); *A61F 2250/0098* (2013.01); *B21J 15/04* (2013.01); *Y10T 29/49993* (2015.01)

(58) Field of Classification Search
CPC ...... A61F 2250/0098; A61F 2002/3008; B21J 15/02; B21J 15/04; B21J 15/14; Y10T 29/49993
USPC ........................................................ 623/1.34
See application file for complete search history.

(56) References Cited

U.S. PATENT DOCUMENTS 6,022,374 A 2/2000 Imran
6,334,871 B1 1/2002 Dor et al.
(Continued)

FOREIGN PATENT DOCUMENTS

EP 2 752 173 7/2014

OTHER PUBLICATIONS

International Search Report and Written Opinion mailed Jul. 28, 2016 in International Patent Application No. PCT/US2016/037009, 11 pages.
(Continued)

*Primary Examiner* — Jermie Cozart
(74) *Attorney, Agent, or Firm* — Squire Patton Boggs (US) LLP

(57) ABSTRACT

A scaffold includes a radiopaque marker connected to a strut. The marker is retained within the strut by a head at one or both ends. The marker is attached to the strut by a process that includes forming a rivet from a radiopaque bead and attaching the rivet to the marker including deforming the rivet to enhance resistance to dislodgement during crimping or balloon expansion. The strut has a thickness of about 100 microns.

21 Claims, 19 Drawing Sheets

(51) Int. Cl.
*A61F 2/89* (2013.01)
*A61F 2/844* (2013.01)
*B21J 15/02* (2006.01)
*B21J 15/14* (2006.01)
*A61F 2/86* (2013.01)
*B21J 15/04* (2006.01)
*A61F 2/30* (2006.01)

(56) References Cited

U.S. PATENT DOCUMENTS

| | | |
|---|---|---|
| 6,506,437 B1 | 1/2003 | Harish et al. |
| 6,918,928 B2 | 7/2005 | Wolinsky et al. |
| 7,625,401 B2 | 12/2009 | Clifford et al. |
| 8,002,817 B2 | 8/2011 | Limon |
| 8,303,644 B2 | 11/2012 | Lord et al. |
| 8,388,673 B2 | 3/2013 | Yang et al. |
| 2001/0027339 A1 | 10/2001 | Boatman et al. |
| 2002/0193862 A1 | 12/2002 | Mitelberg et al. |
| 2003/0060872 A1 | 3/2003 | Gomringer et al. |
| 2004/0027339 A1 | 2/2004 | Schulz |
| 2004/0088039 A1 | 5/2004 | Lee et al. |
| 2005/0004653 A1 | 1/2005 | Gerberding et al. |
| 2005/0283228 A1 | 12/2005 | Stanford |
| 2007/0156230 A1 | 7/2007 | Dugan et al. |
| 2007/0266542 A1* | 11/2007 | Melsheimer ............ A61F 2/91 29/522.1 |
| 2008/0046072 A1 | 2/2008 | Laborde et al. |
| 2012/0042501 A1 | 2/2012 | Wang et al. |
| 2013/0255853 A1 | 10/2013 | Wang et al. |

OTHER PUBLICATIONS

Kajtoch "Strain in the upsetting process", Metalurgy and Foundry Engineering vol. 33, No. 1 (2007).

\* cited by examiner

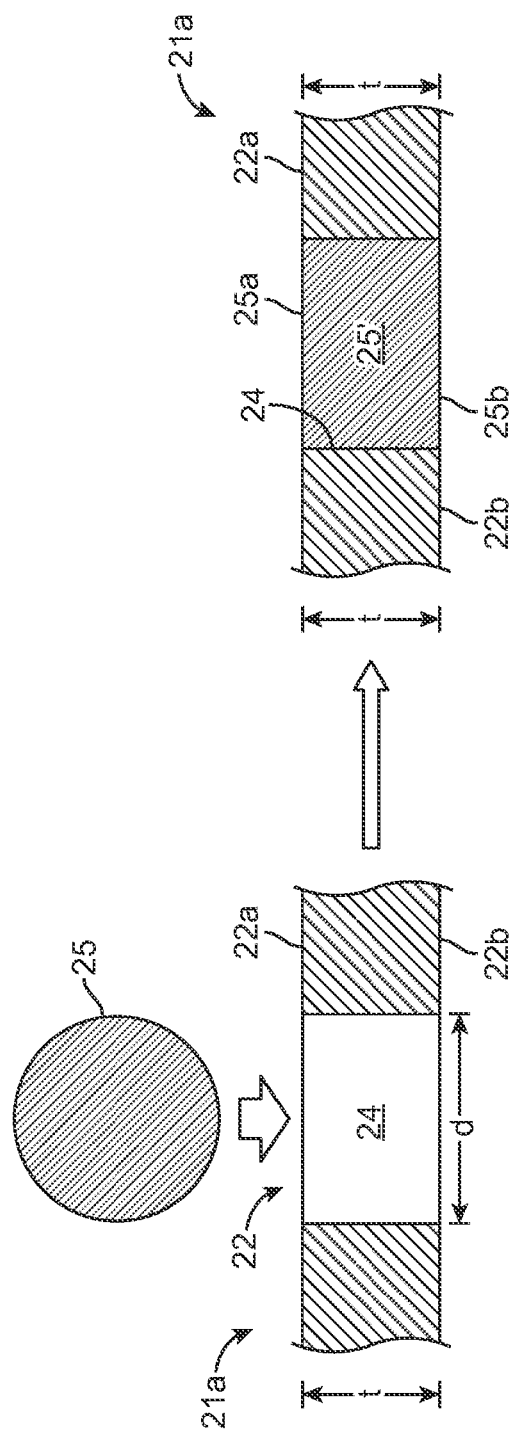

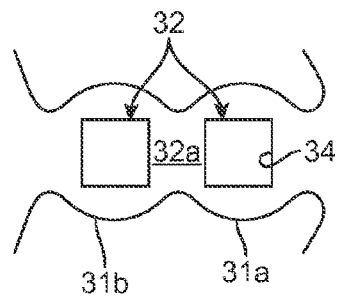 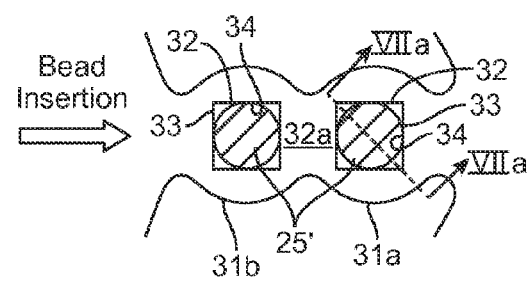
FIG. 4A        FIG. 4B
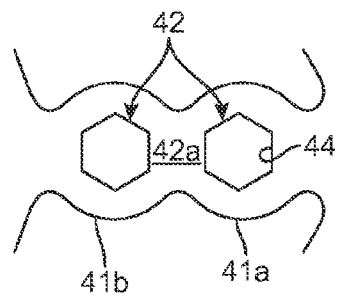 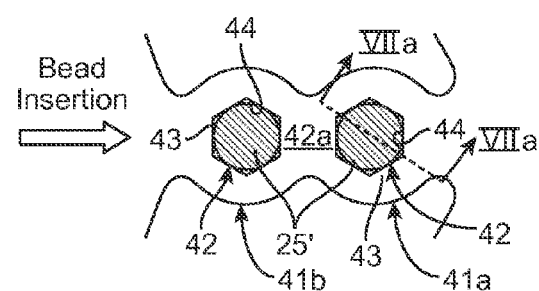
FIG. 5A        FIG. 5B
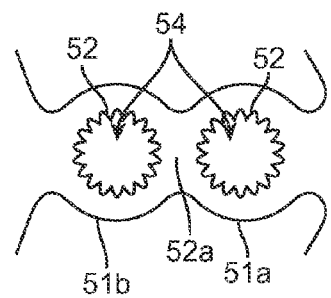 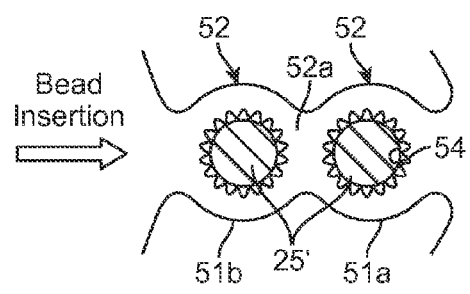
FIG. 6A        FIG. 6B

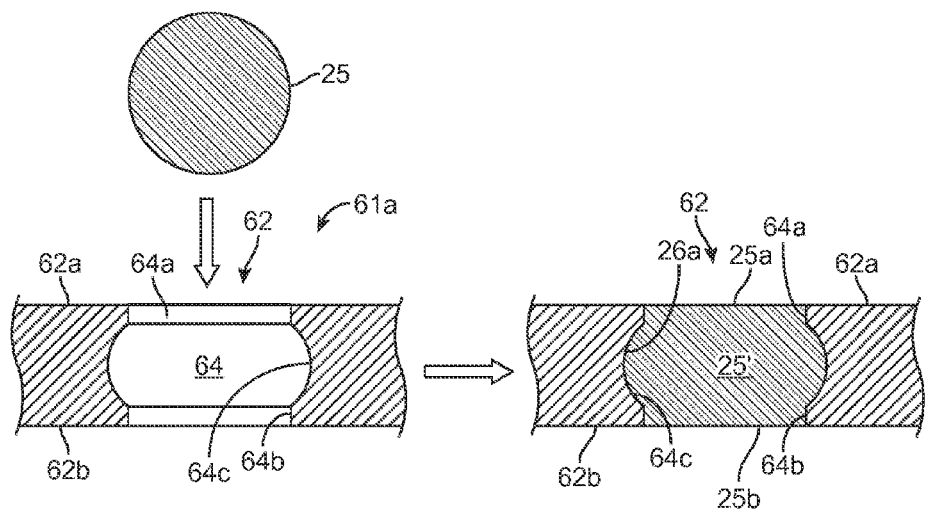
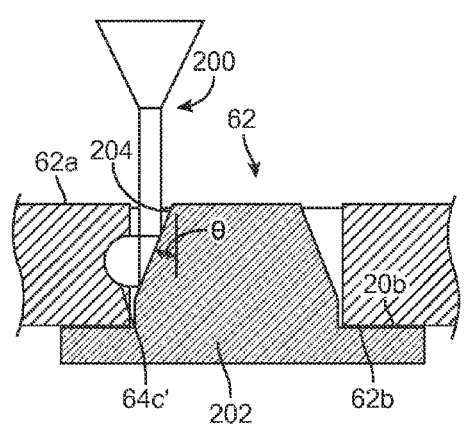
FIG. 8A  FIG. 8B
FIG. 8C

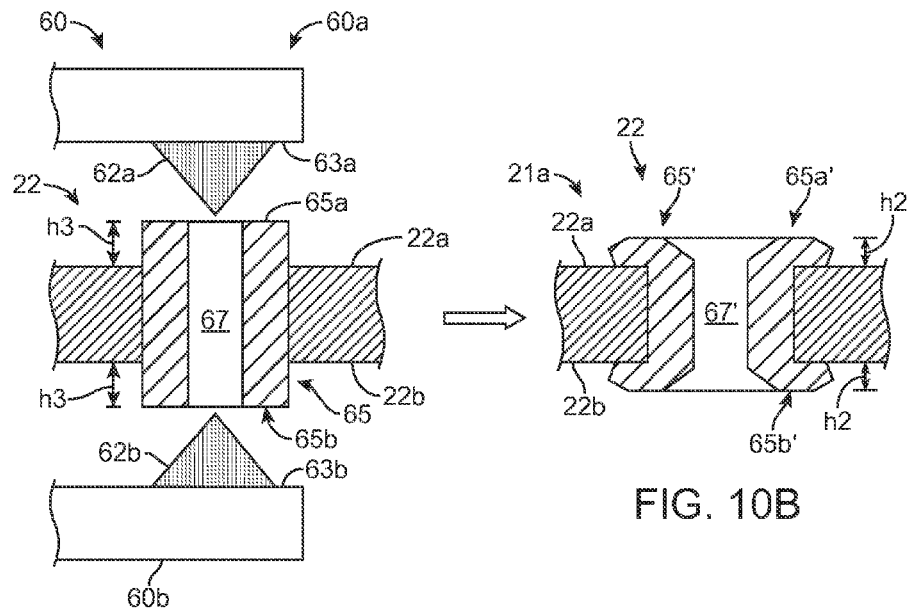
FIG. 10A
FIG. 10B
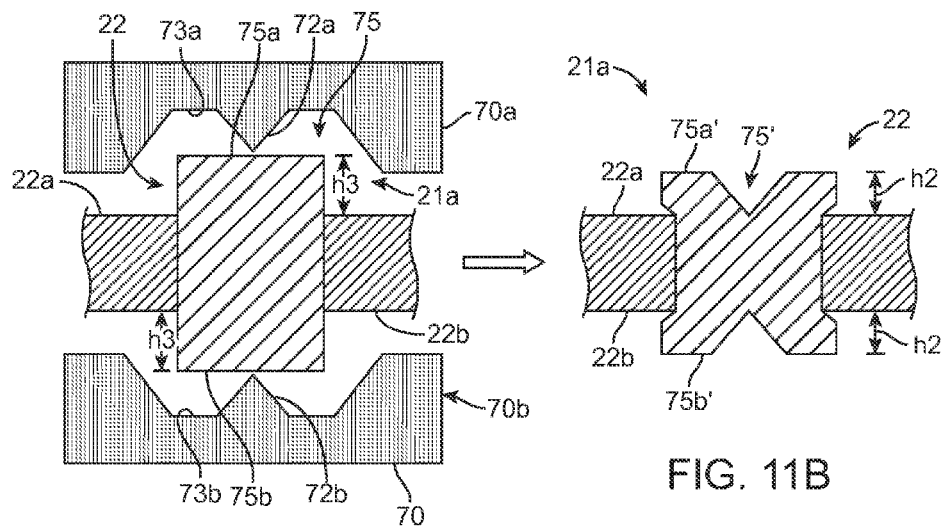
FIG. 11A
FIG. 11B

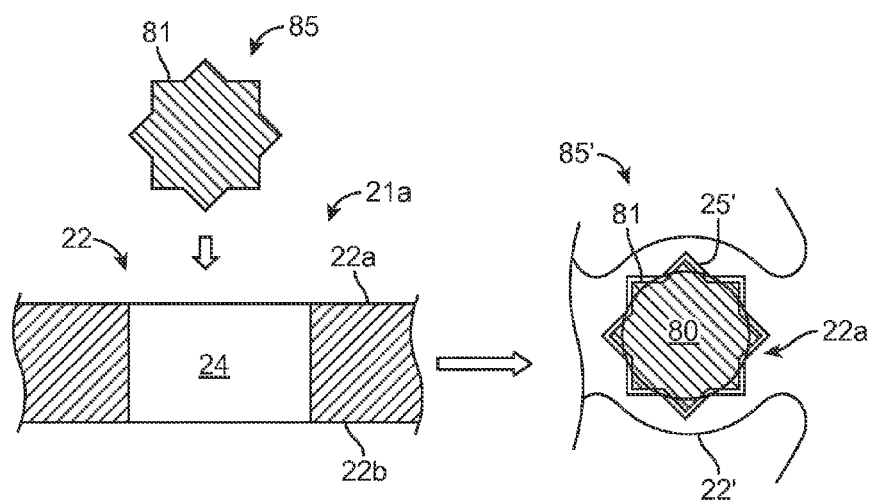
FIG. 12A
FIG. 12B
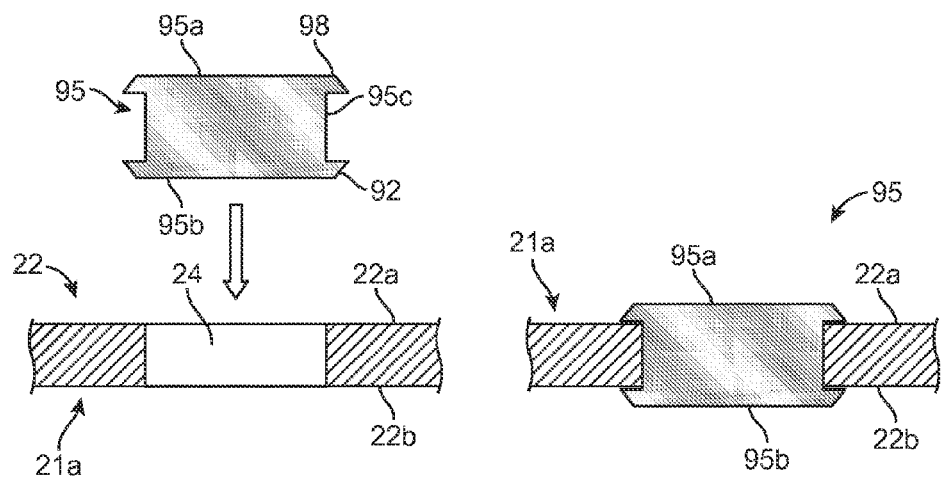
FIG. 13A
FIG. 13B

METHODS FOR ATTACHING A RADIOPAQUE MARKER TO A SCAFFOLD

BACKGROUND OF THE INVENTION

Field of the Invention

The present invention relates to bioresorbable scaffolds; more particularly, this invention relates to bioresorbable scaffolds for treating an anatomical lumen of the body.

Description of the State of the Art

Radially expandable endoprostheses are artificial devices adapted to be implanted in an anatomical lumen. An "anatomical lumen" refers to a cavity, or duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into the anatomical lumen, advancing the catheter in the anatomical lumen to a desired treatment location, expanding the stent at the treatment location, and removing the catheter from the lumen.

The following terminology is used. When reference is made to a "stent", this term will refer to a permanent structure, usually comprised of a metal or metal alloy, generally speaking, while a scaffold will refer to a structure comprising a bioresorbable polymer, or other resorbable material such as an erodible metal, and capable of radially supporting a vessel for a limited period of time, e.g., 3, 6 or 12 months following implantation. It is understood, however, that the art sometimes uses the term "stent" when referring to either type of structure.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or expanded within a lumen (with or without an assisting balloon). Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris-type or other form of crimper, such as the crimping machine disclosed and illustrated in US 2012/0042501. A significant amount of plastic or inelastic deformation occurs both when the balloon expandable stent or scaffold is crimped and later deployed by a balloon. At the treatment site within the lumen, the stent is expanded by inflating the balloon.

The stent must be able to satisfy a number of basic, functional requirements. The stent (or scaffold) must be capable of sustaining radial compressive forces as it supports walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer needed.

Examples of bioresorbable polymer scaffolds include those described in U.S. Pat. No. 8,002,817 to Limon, No. 8,303,644 to Lord, and No. 8,388,673 to Yang. FIG. 1 shows a distal region of a bioresorbable polymer scaffold designed for delivery through anatomical lumen using a catheter and plastically expanded using a balloon. The scaffold has a cylindrical shape having a central axis 2 and includes a pattern of interconnecting structural elements, which will be called bar arms or struts 4. Axis 2 extends through the center of the cylindrical shape formed by the struts 4. The stresses involved during compression and deployment are generally distributed throughout the struts 4 but are focused at the bending elements, crowns or strut junctions. Struts 4 include a series of ring struts 6 that are connected to each other at crowns 8. Ring struts 6 and crowns 8 form sinusoidal rings 5. Rings 5 are arranged longitudinally and centered on an axis 2. Struts 4 also include link struts 9 that connect rings 5 to each other. Rings 5 and link struts 9 collectively form a tubular scaffold 10 having axis 2 represent a bore or longitudinal axis of the scaffold 10. Ring 5*d* is located at a distal end of the scaffold. Crown 8 form smaller angles when the scaffold 10 is crimped to a balloon and larger angles when plastically expanded by the balloon. After deployment, the scaffold is subjected to static and cyclic compressive loads from surrounding tissue. Rings 5 are configured to maintain the scaffold's radially expanded state after deployment.

Scaffolds may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. Scaffolds may also be constructed of bioerodible metals and alloys. The scaffold, as opposed to a durable metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorable or bioresorbable polymer scaffold, as opposed to a metal stent, so that the prosthesis's presence in the vessel is temporary.

Polymeric materials considered for use as a polymeric scaffold, e.g. poly(L-lactide) ("PLLA"), poly(D,L-lactide-co-glycolide) ("PLGA"), poly(D-lactide-co-glycolide) or poly(L-lactide-co-D-lactide) ("PLLA-co-PDLA") with less than 10% D-lactide, poly(L-lactide-co-caprolactone), poly (caprolactone), PLLD/PDLA stereo complex, and blends of the aforementioned polymers may be described, through comparison with a metallic material used to form a stent, in some of the following ways. Polymeric materials typically possess a lower strength to volume ratio compared to metals, which means more material is needed to provide an equivalent mechanical property. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymers such as PLLA or PLGA.

One additional challenge with using a bioresorbable polymer (and polymers generally composed of carbon, hydrogen, oxygen, and nitrogen) for a scaffold structure is that the material is radiolucent with no radiopacity. Bioresorbable polymers tend to have x-ray absorption similar to body tissue. A known way to address the problem is to attach radiopaque markers to structural elements of the scaffold, such as a strut, bar arm or link. For example, FIG. 1 shows a link element 9d connecting a distal end ring 5d to an adjacent ring 5. The link element 9d has a pair of holes. Each of the holes holds a radiopaque marker 11. There are challenges to the use of the markers 11 with the scaffold 10.

There needs to be a reliable way of attaching the markers 11 to the link element 9d so that the markers 11 will not separate from the scaffold during a processing step like crimping the scaffold to a balloon or when the scaffold is balloon-expanded from the crimped state. These two events—crimping and balloon expansion—are particularly problematic for marker adherence to the scaffold because both events induce significant plastic deformation in the scaffold body. If this deformation causes significant out of plane or irregular deformation of struts supporting, or near to markers the marker can dislodge (e.g., if the strut holding the marker is twisted or bent during crimping the marker can fall out of its hole). A scaffold with radiopaque markers and methods for attaching the marker to a scaffold body is discussed in US20070156230.

There is a continuing need to improve upon the reliability of radiopaque marker securement to a scaffold; and there is also a need to improve upon methods of attaching radiopaque markers to meet demands for scaffold patterns or structure that render prior methods of marker attachment in adequate or unreliable.

SUMMARY OF THE INVENTION

What is disclosed are scaffolds having radiopaque markers and methods for attaching radiopaque markers to a strut, link or bar arm of a polymeric scaffold.

According to one aspect markers are re-shaped to facilitate a better retention within a marker hole. Examples include a marker shaped as a rivet.

According to another aspect a hole for retaining the marker is re-shaped to better secure the marker in the hole.

According to another aspect of the invention a scaffold structure for holding a marker and method for making the same addresses a need to maintain a low profile for struts exposed in the bloodstream, while ensuring the marker will be securely held in the strut. Low profiles for struts mean thinner struts or thinner portions of struts. The desire for low profiles addresses the degree thrombogenicity of the scaffold, which can be influenced by a strut thickness overall and/or protrusion from a strut surface. Blood compatibility, also known as hemocompatibility or thromboresistance, is a desired property for scaffolds and stents. The adverse event of scaffold thrombosis, while a very low frequency event, carries with it a high incidence of morbidity and mortality. To mitigate the risk of thrombosis, dual anti-platelet therapy is administered with all coronary scaffold and stent implantation. This is to reduce thrombus formation due to the procedure, vessel injury, and the implant itself. Scaffolds and stents are foreign bodies and they all have some degree of thrombogenicity. The thrombogenicity of a scaffold refers to its propensity to form thrombus and this is due to several factors, including strut thickness, strut width, strut shape, total scaffold surface area, scaffold pattern, scaffold length, scaffold diameter, surface roughness and surface chemistry. Some of these factors are interrelated. Low strut profile also leads to less neointimal proliferation as the neointima will proliferate to the degree necessary to cover the strut. As such coverage is a necessary step to complete healing. Thinner struts are believed to endothelialize and heal more rapidly.

Markers attached to a scaffold having thinner struts, however, may not hold as reliably as a scaffold having thicker struts since there is less surface contact area between the strut and marker. Embodiments of invention address this need.

According to another aspect a thickness of the combined marker and strut is kept below threshold values of about 150 microns while reliably retaining the marker in the hole.

According to another aspect there is a process for forming a rivet and mounting the rivet to a scaffold strut to produce a high resistance to dislodgment of the rivet from the scaffold and avoids complexities associated with orientation and placement of a rivet-shaped bead into a hole having a size of about 250 microns.

According to another aspect there is a process for cold-forming a 203-305 micron (0.008-0.012 inch) diameter platinum bead into the shape of a conventional rivet without losing orientation of the finished rivet. The finished rivet is securely held in a forming die where it can be ejected in a controlled manner into a vacuum pick up tool mounted to a robotic end effector. Cold forming the rivet into a die solves the problem of preserving the orientation of the rivet and eliminates secondary positioning and handling for fitting into the scaffold hole, which is very difficult due to the small size of the finished rivet.

According to another aspect there is a process that allows swaging of a rivet into final position from the abluminal side of a scaffold. The same cold forming method to produce the rivet can be used to swage the rivet and secure it in the scaffold. A stepped mandrel design may be used to hold the scaffold and provide clearance under the rivet which allows swaging the rivet tip on the luminal side of the scaffold. This process creates a trapezoidal or frustoconical shank that secures the rivet to the scaffold. Using this approach allows for automating the rivet manufacturing process and a controlled installation method for swaging the rivet into a polymer scaffold, thereby reducing manufacturing costs and finished product variation.

According to other aspects of the invention, there is a scaffold, medical device, method for making such a scaffold, method of making a marker, attaching a marker to a strut, link or bar arm of a scaffold, or method for assembly of a medical device comprising such a scaffold having one or more, or any combination of the following things (1) through (24):

(1) A method to reduce thrombogenicity, or a scaffold having reduced thrombogenicity, the scaffold comprising a strut, the strut including a strut thickness and a marker attached to the strut, wherein the strut has a thickness (t) and the marker has a length (L, as measured from an abluminal to luminal surface portions of the marker) and is held in the strut, the marker including a portion that protrudes outward from the strut's abluminal and/or luminal surface, wherein the marker length (L) and strut/link/bar arm thickness (t) are related as follows: $1.2 \leq (L/t) \leq 1.8$; $1.1 \leq (L'/t) \leq 1.5$; $1.0 \leq (L/t) \leq 1.8$; and/or $1.0 \leq (L'/t) \leq 1.5$, where L is an undeformed length (e.g., rivet, tube), and L' is a deformed length (e.g. a swaged rivet).

(2) A scaffold comprising a bar arm, link or strut having a hole holding a marker, or a method for making the same according to one or more, or any combination of features described for a Concept E, infra, and with reference to illustrative examples shown in FIGS. 14 through 17, 18A, 18B, 19, 20A, 20B, 21A through 21C and 22A through 22C.

(3) An aspect ratio (AR) of strut width (w) to wall thickness (t) (AR=w/t) is between 0.5 to 2.0, 0.5 to 1.5, 0.7 to 1.5, 0.7 to 1.3, 0.9 to 1.5, 0.9 to 1.2, 1.0 to 1.5, 1.5 to 2.0, or 2.0 to 3.0.

(4) A scaffold comprising a deformed marker secured to a strut, bar arm and/or link, wherein the marker is a rivet pre-made or formed prior to being mounted on a scaffold.

(5) A combined bump (luminal side plus abluminal side, and referring to a portion of a marker and/or polymer at the marker) is no more than a strut or link thickness, e.g., no more than 100 or 85 microns, so that the length at the marker is at most twice a strut or bar arm thickness.

(6) A combined bump (luminal side plus abluminal side, and referring to a portion of a marker and/or polymer at the marker) is at least 10-50% more than a thickness of a strut or bar arm at the marker.

(7) A wall thickness for a scaffold (before-crimp diameter of 3 to 5 mm) is less than 150 microns, less than 140 microns, less than 130 microns, about 100 micron, 80 to 100 microns, 80 to 120 microns, 90 to 100 microns, 90 to 110 microns, 110 to 120 microns, or 95 to 105 microns. More preferably a wall thickness is between 80 and 100 microns, and more preferably between 85 and 95 microns; and (8) A wall thickness for a scaffold (before-crimp diameter of 7 to 10 mm) is less than 280 microns, less than 260 microns, less than 240 microns, about 190 micron, 149 to 186 microns, 149 to 220 microns, 170 to 190 microns, 170 to 210 microns, 210 to 220 microns. More preferably a wall thickness is between 150 and 190 microns for a scaffold having an outer diameter of 7, 8 or 9 mm.

(9) A polymeric scaffold is heated about 0-20 degrees above its Tg during or after marker placement and prior to crimping, such as prior to and within 24 hours of crimping; wherein the heating improves a retention force maintaining a marker in a hole.

(10) The radiopaque marker is comprised of platinum, platinum/iridium alloy, iridium, tantalum, palladium, tungsten, niobium, zirconium, iron, zinc, magnesium, manganese or their alloys.

(11) A process for attaching a radiopaque marker including pressing a bead into a die to form a radiopaque rivet, removing the rivet from the die using a tool connected to a head of the rivet and while the head remains connected to the tool, placing the rivet within a scaffold hole, wherein the rivet orientation is maintained from the time it is removed from the die to when it is placed in the hole.

(12) A rivet locked in a strut of a scaffold by swaging, the rivet having a mechanical locking angle $\theta$ such as the locking angle $\theta$ in FIGS. 22A-22B.

(13) A process for attaching a marker to a scaffold, including deforming the marker between a first and second ram head, wherein the coefficient of friction (Mu) between the head and marker surface on one side is higher than Mu on the opposite side; for example, $Mu>0.17$ on one side and $Mu<0.17$ on the other side.

(14) A rivet mounted to a scaffold and satisfying a minimum distance of at least one of $\delta 1$, $\delta 2$ and $\delta 3$ with respect to a strut rim structure as discussed in connection with FIG. 16.

(15) A marker engaged with a scaffold hole, the marker including a shank shaped as a frustum engaged with the hole and a head disposed on the outer surface.

(16) A tapered marker hole, or a hole having one of a luminal and abluminal opening is greater than the other.

(17) A method for attaching a non-spherical marker to a hole, including forming a spherical bead into a rivet and lifting from the die and placing into the hole the formed rivet using a tool to maintain the orientation of the rivet marker.

(18) A method for making a medical device, including using a polymer scaffold including a strut having a hole formed in the strut, wherein the strut has a thickness of between 80 and 120 microns measured between a first side of the strut and a second side of the strut and the strut comprises poly(L-lactide); and using a radiopaque rivet marker having a head and a shank; and placing the rivet into the hole so that the head is disposed on a first surface of the first side of the strut; and swaging the rivet including making a deformed shank from the rivet shank while the rivet sits in the hole; wherein the head resists a first push-out force acting on the first surface by the head interfering with the first side of the hole; and wherein the deformed shank resists a second push-out force acting on a second surface of the second side of the strut by the deformed shank interfering with the second side of the hole.

(19) The method of item (18) including one or more of, or combination of the following things: wherein the deformed shank has a flange disposed on the second surface; wherein the first surface is one of a luminal and abluminal surface of the scaffold and the second surface is one of the other of the luminal and abluminal surface; the method further comprising using a rivet having a shank length greater than the strut thickness such that a shank portion extends out from the hole's second side when the rivet is in the hole, and the swaging step makes the flange from the shank portion extending out from the second side; the method further comprising using a rivet having a shank length greater than the strut thickness such that a shank portion extends out from the hole's second side when the rivet is in the hole, wherein the shank is a cylinder, and wherein the deformed shank is a frustum; wherein the head is disposed at a first opening of the first side of the hole and a base of the frustum is disposed at a second opening of the second side of the hole, and wherein the swaging step makes the second opening larger than the first opening; wherein the deformed shank has a first end proximal of the head and a second end distal of the head, the first end is disposed at a first opening of the hole and the second end is disposed at a second opening of the hole, wherein prior to the swaging step the first and second ends have the same diameter, and wherein the swaging step deforms the second opening and the second end such that the second end and second opening are larger than the first end and the first opening, respectively; wherein the marker rivet has an undeformed length (L) before swaging, a deformed length (L') after swaging, and L, L' and the strut thickness (t) are related by $t \times (1.2) \le L \le t \times (1.8)$ and $1.2 \le (L/t) \le 1.8$; and $t \times (1.1) \le L' \le t \times (1.5)$ and $1.1 \le (L'/t) \le 1.5$; wherein the scaffold strut comprises poly(L-lactide); wherein the scaffold is made from a polymer having a glass transition temperature (Tg), wherein the polymeric scaffold is heated 0-20 degrees above its Tg after the marker rivet is deformed; and/or wherein the rivet is comprised of platinum, platinum/iridium alloy, iridium, tantalum, palladium, tungsten, niobium, zirconium, iron, zinc, magnesium, manganese or their alloys.

(20) A process for attaching a radiopaque material to a polymeric scaffold, comprising: using a die, deforming a spherical bead into a rivet having a head and shank, the bead comprising the radiopaque material; attaching a tool to the rivet head, including creating a pressure difference at a tip of the tool to adhere the rivet head to the tool tip thereby enabling the tool to lift and remove the rivet from the die and maintain an orientation of the rivet relative to the tip; removing the rivet from the die using a tool; without removing the rivet from the tip of the tool, placing the rivet into a hole of the scaffold wherein the orientation of the rivet relative to the tool tip to enable placement of the shank into the hole; wherein following the placing step the rivet head rests on one of a luminal and abluminal surface of the strut and a tail of the shank extends out from the other of the luminal and abluminal surface; and forming an interference fit between the rivet and hole including deforming the tail.

(21) The method of item (20) including wherein the die comprises a plate having a hole and a counter bore; wherein the die comprises a plate having a tapered hole, such that the shank of the rivet is tapered; wherein the scaffold has a strut thickness and a shank of the rivet has a length that is between 125% and 150% of the strut thickness; wherein the hole is a tapered hole after forming the interference fit; wherein the forming step includes deforming a shank of the rivet into a frustum; wherein the hole is a polygonal hole or an elliptical hole; and/or wherein the tool comprises a vacuum tip configured for grabbing the head of the rivet and releasing the head therefrom by modifying a gas pressure at the tip.

(22) A medical device, comprising: a scaffold having a thickness and a pattern of elements forming a tubular body, the elements comprising rings interconnected by links, wherein at least one of the links comprises: a hole, and a rim substantially circumscribing the hole and defining a hole wall and a strut rim, wherein a distance between the wall and rim is D; a radiopaque marker disposed in the hole, the marker including a head having a flange disposed on the rim; wherein the flange has a radial length of between ½ D and less than D; wherein the scaffold thickness (t) is related to a length (L) of the marker measured between an abluminal and luminal surface of the marker by $1.1 \le (L/t) \le 1.8$.

(23) A radiopaque marker constructed according to Concept A, Concept B, Concept C, Concept D, Concept E, Concept F, Concept G or combinations thereof.

(24) A radiopaque marker and scaffold link / strut having a hole to receive the marker, and having a high resistance to dislodgment according to one or more of, or any combination of Concepts A, B, C, and/or D combined with the marker according to Concept E.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 2A is a partial side-cross sectional view of the link of FIG. 2 taken at section IIA-IIA with a spherical marker being placed in the hole.

FIG. 2B shows the link of FIG. 2A after the marker is placed in the hole.

FIGS. 4A, 4B, 5A and 5B are top views of a link and marker according to another embodiment.

FIGS. 6A and 6B are top views of a link and marker according to another embodiment.

FIG. 8A is a partial side-cross sectional view of a link according to another embodiment. A spherical marker is being placed in a hole of the link.

FIG. 8B shows the link of FIG. 8A after the marker is placed in the hole.

FIG. 8C shows a method for making the hole of FIG. 8A.

FIGS. 10A-10B are cross-sectional views of a link and marker and method of attaching the marker to the link according to another embodiment.

FIGS. 11A-11B are cross-sectional views of a link and marker and method of attaching the marker to the link according to another embodiment.

FIGS. 12A-12B are cross-sectional views of a link and marker and method of attaching the marker to the link according to another embodiment.

FIGS. 13A-13B are cross-sectional views of a link and marker and method of attaching the marker to the link according to another embodiment.

DETAILED DESCRIPTION

Figure 1:
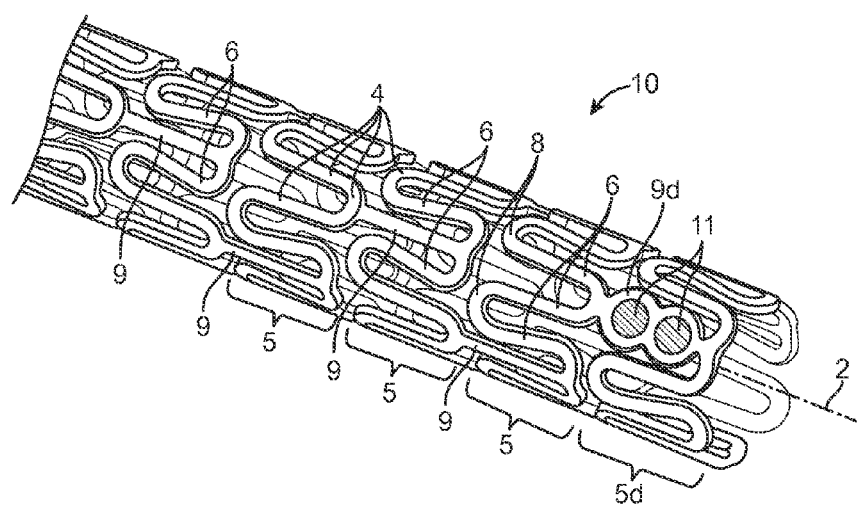
FIG. 1 is a perspective view of a portion of a prior art scaffold. The scaffold is shown in a crimped state (balloon not shown).

In the description like reference numbers appearing in the drawings and description designate corresponding or like elements among the different views.

For purposes of this disclosure, the following terms and definitions apply:

The terms "about," "approximately," "generally," or "substantially" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance or standard deviation from d1.

It is understood that any numerical value, range, or either range endpoint (including, e.g., "approximately none", "about none", "about all", etc.) preceded by the word "about," "approximately," "generally," or "substantially" in this disclosure also describes or discloses the same numerical value, range, or either range endpoint not preceded by the word "about," "approximately," "generally," or "substantially."

A "stent" means a permanent, durable or non-degrading structure, usually comprised of a non-degrading metal or metal alloy structure, generally speaking, while a "scaffold" means a temporary structure comprising a bioresorbable or biodegradable polymer, metal, alloy or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the inner diameter or the outer diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon (i.e., a balloon having a 6.5 mm nominal diameter when inflated to a nominal balloon pressure such as 6 times atmospheric pressure) has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

When reference is made to a diameter it shall mean the inner diameter or the outer diameter, unless stated or implied otherwise given the context of the description.

When reference is made to a scaffold strut, it also applies to a link or bar arm.

"Post-dilation diameter" (PDD) of a scaffold refers to the inner diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "before-crimp diameter" means an outer diameter (OD) of a tube from which the scaffold was made (e.g., the scaffold is cut from a dip coated, injection molded, extruded, radially expanded, die drawn, and/or annealed tube) or the scaffold before it is crimped to a balloon. Similarly, a "crimped diameter" means the OD of the scaffold when crimped to a balloon. The "before-crimp diameter" can be about 2 to 2.5, 2 to 2.3, 2.3, 2, 2.5, 3.0 times greater than the crimped diameter and about 0.9, 1.0, 1.1, 1.3 and about 1-1.5 times higher than an expanded diameter, the nominal balloon diameter, or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown in the case of a stent or scaffold that has an undulating ring pattern, e.g., FIG. 1. When the scaffold is deployed or expanded by the balloon, the inflated balloon plastically deforms the scaffold from its crimped diameter. Methods for crimping scaffolds made according to the disclosure are described in US20130255853.

A material "comprising" or "comprises" poly(L-lactide) or PLLA includes, but is not limited to, a PLLA polymer, a blend or mixture including PLLA and another polymer, and a copolymer of PLLA and another polymer. Thus, a strut comprising PLLA means the strut may be made from a material including any of a PLLA polymer, a blend or mixture including PLLA and another polymer, and a copolymer of PLLA and another polymer.

Bioresorbable scaffolds comprised of biodegradable polyester polymers are radiolucent. In order to provide for fluoroscopic visualization, radiopaque markers are placed on the scaffold. For example, the scaffold described in U.S. Pat. No. 8,388,673 ('673 patent) has two platinum markers 206 secured at each end of the scaffold 200, as shown in FIG. 2 of the '673 patent.

Figure 2:
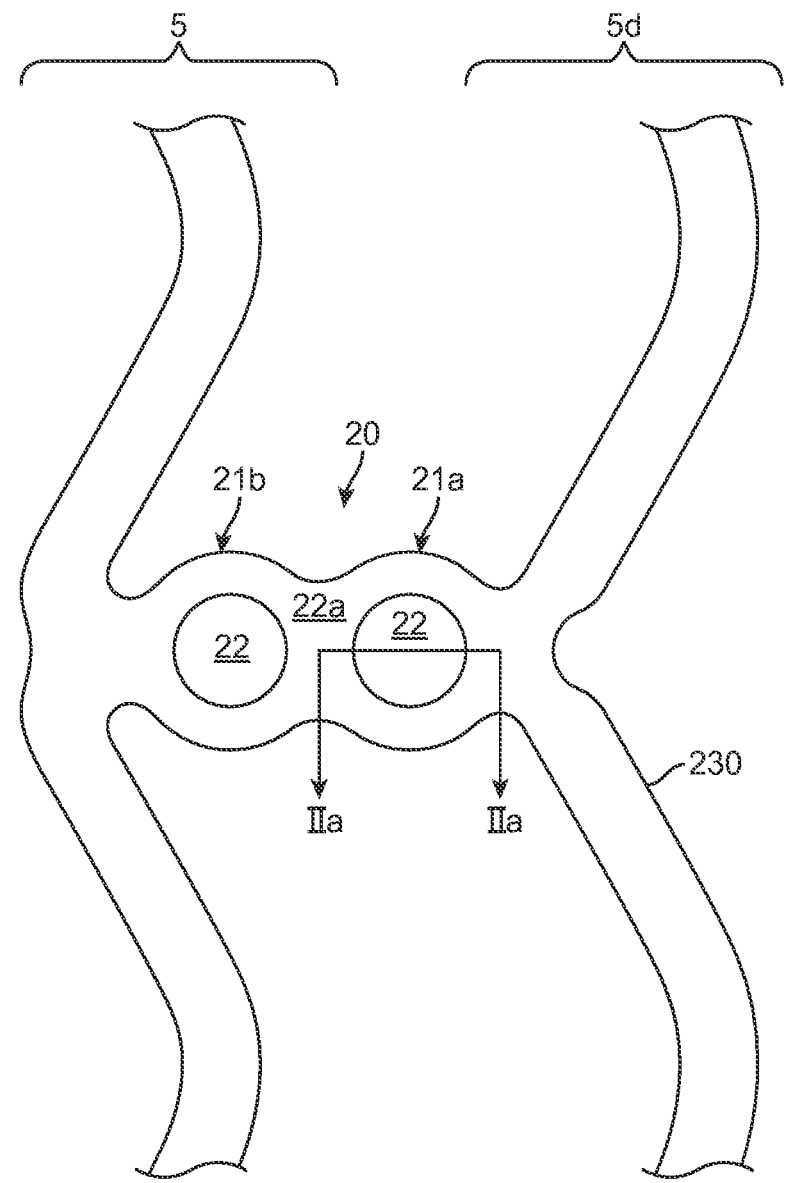
FIG. 2 is a top partial view of a scaffold showing a link connecting adjacent rings. The link includes holes for holding markers.

FIG. 2 is a top planar view of a portion of a polymer scaffold, e.g., a polymer scaffold having a pattern of rings interconnected by links as in the case of the '673 patent embodiments. There is a link strut 20 extending between rings 5d, 5 in FIG. 2. The strut 20 has formed left and right structures or strut portions 21b, 21a, respectively, for holding a radiopaque marker. The markers are retainable in holes 22 formed by the structures 21a, 21b. The surface 22a corresponds to an abluminal surface of the scaffold. An example of a corresponding scaffold structure having the link 20 is described in FIGS. 2, 5A-5D, 6A-6E and col. 9, line 3 through col. 14, line 17 of the '673 patent. The embodiments of a scaffold having a marker-holding link structure or method for making the same according to this disclosure in some embodiments include the embodiments of a scaffold pattern according to FIGS. 2, 5A-5D, 6A-6E and col. 9, line 3 through col. 14, line 17 of the '673 patent.

Figure 15:
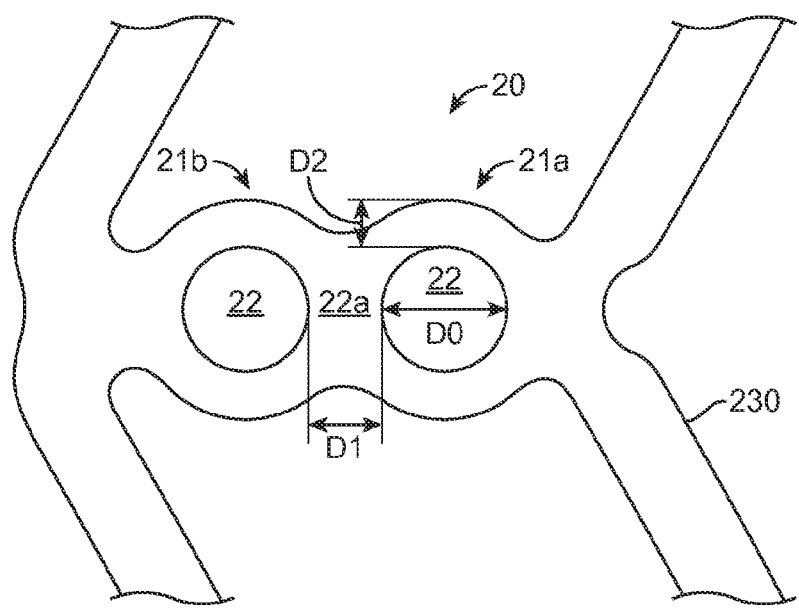
FIG. 15 is a reproduction of FIG. 2 showing additional dimensional characteristics and/or feature of the bar arm, link or strut for holding two markers.

FIG. 15 is a reproduction of FIG. 2 illustrating additional dimensional features, specifically characteristic dimensional features D0, D1 and D2. The diameter of the hole 22 is D0. The distance between the adjacent holes 22 is greater than or equal to D1. And the brim width of either or both holes 22, or distance from the inner wall surface circumscribing either or both holes 22 to the edge of the link 20 is greater than or equal to D2.

Figure 14:
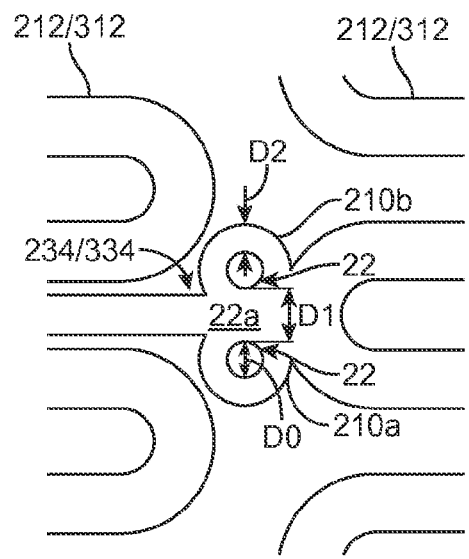
FIG. 14 shows a portion of a scaffold pattern including holes for receiving markers according to the disclosure. The scaffold is in a crimped state.

With reference to FIG. 14, in an alternative embodiment the holes for receiving markers are circumferentially offset form each other (FIG. 15 illustrates marker holes axially offset from each other). The structure depicted in FIG. 14 is a top planar view of a portion of a polymer scaffold pattern, e.g., a polymer scaffold having a pattern of rings interconnected by links disclosed in any of the embodiments described in FIGS. 2, 3, 4, 5A, 5B, 6A, 6B, 9A and 9B and the accompanying paragraphs [0130]-[0143], [171]-[0175] of US20110190871 ('871 Pub.). In this view the scaffold is configured in a crimped configuration. There is a link strut 234/334 extending between rings 212/312 in FIG. 14. The strut 20 has formed upper and lower structures or strut portions 210b, 210a, respectively, for holding a radiopaque marker. The markers are retainable in holes 22 formed by the structures 210a, 210b. The surface 22a corresponds to an abluminal surface of the scaffold. The embodiments of a scaffold having a marker-holding link structure or method for making the same according to this disclosure in some embodiments include any of the embodiments described in FIGS. 2, 3, 4, 5A, 5B, 6A, 6B, 9A and 9B and the accompanying paragraphs [0130]-[0143], [0171]-[0175] of US20110190871 ('871 Pub).

Additional scaffold structure considered within the scope of this disclosure is the alternative scaffold patterns having the marker structure for receiving markers as described in FIGS. 11A, 11B and 11E and the accompanying description in paragraphs [0177]-[0180] of the '871 Pub. In these embodiments the values D0, D1 and D2 would apply to the relevant structure surrounding the holes 512, 518 and 534 shown in the '871 Pub., as will be readily understood.

One method for marker placement forces a spherical-like body into a cylindrical hole. This process is illustrated by FIGS. 2A and 2B. Shown in cross-section is the hole 22 and surrounding structure of the link portion 21a as seen from Section IIa-IIa in FIG. 2. The hole 22 extends through the entire thickness (t) of the strut portion 21a and the hole 22 has an about constant diameter (d) from the luminal surface 22b to the abluminal surface 22a. A generally spherical marker 25 is force-fit into the hole 22 to produce the marker 25' in the hole 22 illustrated in FIG. 2B. The spherical marker 25 has a volume about equal to, less than or greater than the volume of the open space defined by the plane of the abluminal surface 22a, the plane of the luminal surface 22b and the generally cylindrical walls 24 of the hole 22. The spherical body is reshaped into body 25' by the walls 24 and applied forces applied to each side of the body (e.g., placing the scaffold on a mandrel and pressing into the sphere to force it into the hole using a tool. The deformed shape 25' may be achieved by using one or two rollers pressed against the sphere 25 when it is disposed within the hole 22. The rollers (not shown) are pressed against each side of the marker 25 to produce the deformed marker 25' structure shown in FIG. 2B. Alternatively, the marker 25 may be held on a tip of a magnetized, or vacuum mandrel and pressed (from the abluminal surface 22a side) into the hole 22 while a non-compliant flat surface is pressed into the marker from the luminal side 22b. Referring to FIG. 2B, the marker 25' has an abluminal surface 25a that is about flush with surface 22a and luminal surface 25b that is about flush with surface 22b. Methods for placing the marker 25 in the hole 22 are discussed in US20070156230.

According to one example, the hole 22 has a hole diameter (d) of 233.7 μm and an average initial spherical marker size (Johnson-Matthey marker beads) of 236.7 μm. The thickness (t) is 157.5 microns and hole 22 volume is $t \times \pi d^2 = 6.76E6$ μm³. The average spherical volume size is 6.94E6 μm³. Hence, in this embodiment when the spherical marker 25 is press-fit into the hole 22, the marker 25 is deformed from a generally spherical shape into more of a cylindrical shape. In some embodiments an average volume size for the marker 25 may be only slightly larger in volume (3%) than a hole 22 volume. Larger beads presumably stretch the marker brim while smaller beads will contact the walls 24 when deformed, but do not fill the hole 22 volume completely. As would be understood, the about flush with the luminal and abluminal surfaces accounts for the variances in marker 25 volume size from the manufacturer and volume size variances of the hole 22 volume.

TABLE 1 contains a theoretical volume of an average spherical platinum marker 25 relative to that of the hole 22 for a Scaffold A and a Scaffold B.

TABLE 1

Marker and Hole Dimensions

| Scaffold | Strut Thickness (μm) | Marker Hole Diameter (μm) | Average Marker Diameter (μm) | Idealized Marker Hole Volume (μm³) | Average Marker Volume (μm³) |
|---|---|---|---|---|---|
| A | 157.5 | 233.7 | 236.7 | 6.76E6 | 6.94E6 |
| B | 100 | 241.3 | 236.7 | 4.57E6 | 6.94E6 |

The larger the marker volume is relative to the hole volume, the more the marker brim or space 22 must increase in size if the marker 25' will be flush with the surfaces 22a, 22b. Otherwise, if the volume for the hole 22 does not increase marker material would be left protruding above and/or below the hole 22.

With respect to the different thickness struts of Scaffold A and Scaffold B (TABLE 1) it will be appreciated that an acceptable marker 25 fitting method and/or structure for Scaffold A (thick struts) may not be acceptable for Scaffold B (thin struts). It may be necessary to change the volume and/or shape size of the hole and/or marker, and/or method of attachment of the marker to a hole when a strut thickness is reduced in size, e.g., when there is an about 37% reduction in strut thickness.

There are several dimensional parameters that result in a physical interaction between the strut walls 24 and marker 25 surface sufficient to keep the marker in the hole 25 during scaffold manipulations, such as drug coating, crimping and scaffold expansion. Factors (1)-(3) that affect the physical securement of the marker 25' in the hole 22 include:

(1) The interference fit between the marker 25' and the inside surface or brim 24 of the marker hole 22. This fit is a function of
   The total contact area between the marker 25' and the polymer walls or brim 24.
   The residual stresses in the marker brim 24 polymer and 25' that results in a compressive or hoop stress between the marker brim 24 and marker 25'.
(2) The roughness of the marker 25' surface and surface of the brim 24, or coefficient of static friction between the contacting marker and wall surfaces.
(3) Where a drug-polymer coating is applied (not shown in FIG. 2B), the gluing-in effect of the drug/polymer coating. The contribution of this coating to marker 25' retention comes down to the fracture strength of the coating on the abluminal or luminal surfaces 22a, 22b as the coating must fracture through its thickness on either side for the marker 25' to become dislodged.

With respect to factor (3), in some embodiments an Everolimus/PDLLA coating is applied after the marker 25' is fit in place. This type of coating can seal in the marker 25. However, an Everolimus /PDLLA coating tends to be thin (e.g., 3 microns on the abluminal surface 22a and 1 micron on the luminal surface 22b), which limits it's out of plane shear strength resisting dislodgment of the marker from the hole.

In some embodiments a polymer strut, bar arm and/or link has a thickness about, or less than about 100 microns, which is less than the wall thickness for known scaffolds cut from tubes. There are several desirable properties or capabilities that follow from a reduction in wall thickness for a scaffold strut; for example, a reduction from the Scaffold A wall thickness to Scaffold B wall thickness. The advantages of using the reduced wall thickness include a lower profile and hence better deliverability, reduced acute thrombogenicity, and potentially better healing. In some embodiments the Scaffold B (100 micron wall thickness) has a pattern of rings interconnected by struts as disclosed in the '673 patent.

In some embodiments it is desirable to use the same size marker 25 for Scaffold B as with Scaffold A, so that there is no difference, or reduction, in radiopacity between the two scaffold types. Reducing the strut thickness, while keeping the marker hole 22 the same size can however result in the marker protruding above and/or below the strut surfaces due to the reduced hole volume. It may be desirable to keep the abluminal and luminal surfaces 25a, 25b of the marker 25' flush with corresponding surfaces 22a, 22b for Scaffold B, in which case the hole 22 diameter (d) may be increased to partially account for the reduced hole volume resulting from the thinner strut. This is shown in TABLE 1 for Scaffold B, which has a hole diameter greater than the hole diameter for Scaffold A.

With respect to the Factors (1)-(3) it will be appreciated that the substantially frictional force relied on to resist dislodgement of the marker 25' from the hole 22 reduces as the strut thickness is reduced. When using a fixed sized marker of constant volume, and assuming the marker fills a cylindrical hole, the contact area between the marker and hole sidewall may be expressed in terms of a marker volume and strut thickness, as in EQ. 1.

$$A = 2(\pi t V)^{1/2} \quad (EQ. 1)$$

Where
A=Contact area between marker hole sidewall and marker
t=Strut thickness
V=marker volume EQ. 1 shows that in a limiting case of the strut 21a thickness becoming very thin (t→0), the marker 25' becomes more and more like a thin disc, which would have minimal mechanical interaction with the wall 24. Hence the frictional forces between the marker 25' and wall 24 decreases because the contact area is reduced. Comparing Scaffold A with Scaffold B, the marker 25' retention force in the hole 22 therefore becomes worse due to the about 37% reduction in strut thickness. Indeed, it may be expected that frictional forces that hold the marker 25' in the hole reduce by about 20%, which 20% reduction is the surface area reduction of the walls 24 when the strut thickness is reduced by the about 37% (Scaffold A→Scaffold B). This assumes the coefficients of static friction and level of residual hoop stress are otherwise unchanged between Scaffold A and B.

According to another aspect of the disclosure there are embodiments of a strut having a hole for holding a radiopaque marker and methods for securing a marker to a strut. The embodiments address the ongoing need for having a more secure attachment of a marker to a polymer strut. In preferred embodiments the polymer strut has a thickness, or a scaffold comprising the strut is cut from a tube having a wall thickness less than about 160 μm or 150 μm, a wall thickness of about 100 μm or a wall thickness less than 100 μm and while retaining the same size marker as a strut having a thickness between 150-160 μm, so that the radiopacity of the scaffold does not change.

An improved securement of a marker to a hole according to the disclosure includes embodiments having one or more of the following Concepts A through G:

A. Following marker insertion a sealing biodegradable polymer is applied to secure the marker in place (Concept A).
B. The strut hole is made in an irregular shape to increase an adhesive and mechanical locking effect of a scaffold coating (Concept B).

C. The marker has roughened surfaces to increase the coefficient of friction between the polymer walls and marker (Concept C).
D. The holes are made concave to increase the contact area and/or to provide a mechanical engagement between the marker and the hole (Concept D).
E. Radiopaque markers shaped like, or usable as rivets are attached to the hole (Concept E).
F. Polygonal or Irregular markers (Concept F).
G. Snap-in markers (Concept G).

Figure 3A:
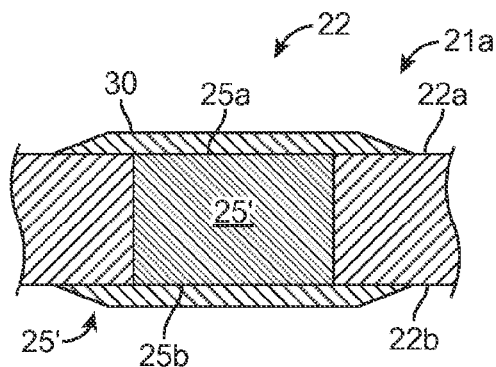
FIGS. 3A-3C are cross sectional views of the link and marker of FIG. 2B according to one embodiment.
Figure 3B:
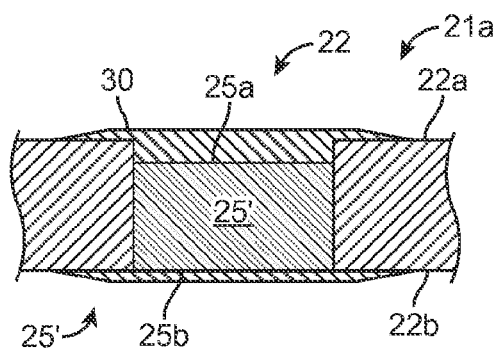
Figure 3C:
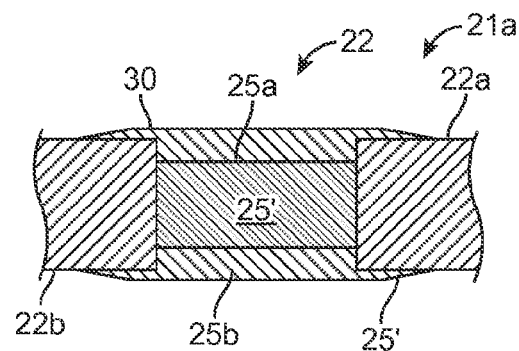

According to Concept A, sealing layers of polymer 30 are applied to the abluminal and/or luminal surfaces 22a, 22b of the strut 21a near the marker 25' and luminal and abluminal surfaces 25a, 25b surfaces of the marker 25' as shown in FIGS. 3A-3C. The amount of sealing polymer 30 applied on the marker 25 may be significant but without creating an unsatisfactory bump or protrusion on the abluminal or luminal surfaces. To increase the available space for the sealing polymer (without reducing the marker size or creating a large bump on the surface) the hole 22 may be made wider, so that the marker 25 when pressed and deformed into the hole 22 is recessed from the abluminal surface 22a and/or abluminal surface 22b. This is shown in FIGS. 3B and 3C. In FIG. 3B the marker 25' is recessed from the side 22a but flush with 22b. In FIG. 3C the marker 25' is recessed on both surfaces.

The sealing polymer 30 may be applied in different ways. One approach is to apply a small amount of solution consisting of a biodegradable polymer dissolved in solvent. This can be done with a fine needle attached to a microsyringe pump dispenser. The solution could be applied to both the abluminal and luminal surfaces of the marker and marker brim portions of the hole 22 (FIGS. 3A-3C). Suitable polymers include poly(L-lactide) ("PLLA"), poly(D,L-lactide-co-glycolide) ("PLGA"), poly(D-lactide-co-glycolide), poly(D,L-lactide) ("PDLLA") poly(L-lactide-co-caprolactone) ("PLLA-PCL") and other bioresorbable polymers. Solvents include chloroform, acetone, trichloroethylene, 2-butanone, cyclopentanone, ethyl acetate, and cyclohexanone.

Alternatively, the sealing polymer may be applied in a molten state. As compared to the solvent application embodiment of the sealing polymer, a polymer applied in the molten state may produce a more sizable bump or protrusion on the abluminal and/or luminal surface 22a, 22b. While avoidance of bumps on these surfaces is generally of concern, small bumps or protrusions are acceptable if they are less than the strut thickness. For example, in some embodiments the bump is less than about 100 microns, or about 85 microns (combined bumps on luminal and abluminal sides). Thus the length of the marker (L' or L) may be up to about 100 or 85 microns higher than the strut thickness, as in a strut thickness of about 100 or 85 microns.

According to Concept B, the marker hole 22 is modified to increase the adhesive effect of a drug/polymer coating on increasing the marker retention. If larger gaps are made between the marker 25 and wall 24 of the hole 22 more of the coating can become disposed between the marker 25' and wall 24 of the hole 22. The presence of the coating in this area (in addition to having coating extending over the surfaces 22a, 25a, 22b and 25a) can help to secure the marker 25 in the hole because the surface area contact among the coating, wall 24 and marker 25 is increased. Essentially, the coating disposed within the gaps between the wall 24 and marker 25 can perform more as an adhesive. In addition, the coating filling in around the deformed marker bead can improve retention via mechanical interlocking.

Gaps can be made by forming the hole with rectangular, hexagonal or more generally polygonal sides as opposed to a round hole. When a spherical marker 25 is pressed into a hole having these types of walls there will be gaps at each wall corner.

FIGS. 4A and 4B show modified marker-holding strut portions 31a, 31b before and after, respectively, a marker 25 is pressed into each hole 32 of the strut portions 31a, 31b. The holes 32 are formed as rectangular holes. Since there are four sides 34 to a rectangular, there are four corners to the hole 32. As can be appreciated from FIG. 4B there are four gaps 33 between the hole walls 34 and the bead 25'. The gaps 33 are present at each wall corner of the rectangular hole 32.

FIGS. 5A and 5B show modified marker-holding strut portions 41a, 41b before and after, respectively, a marker 25 is pressed into each hole 42 of the strut portions 41a, 41b. The holes 42 are formed as hexagonal holes. Since there are six sides 44 to a hexagon, there are six corners to the hole 42. As can be appreciated from FIG. 5B there is at least one and up to six gaps 43 between the hole walls 44 and the marker 25'.

Figure 7A:
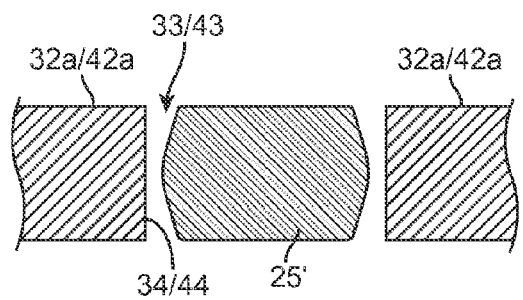
FIGS. 7A-7B are cross sectional views of the link and marker according to any of the embodiments of FIGS. 4A, 4B, 5A and 5B.
Figure 7B:
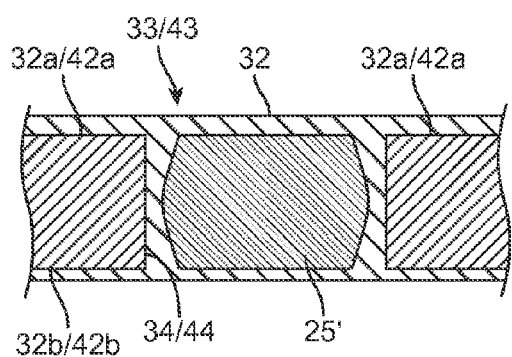

Referring to FIGS. 7A and 7B there is shown cross-sectional side-views of the holes 32 and 42 with the marker 25' in the hole. The view of FIG. 7A is taken from section VIIa-VIIa in FIGS. 4B and 5B. As shown there is the gap 33, 43 present at the corner, which provides space for the polymer coating 32 (FIG. 7B) to lodged when the coating is applied to the scaffold. The coating 32 is disposed between the surface of the marker 25' and wall 34, 44 of the hole 32, 42 combined with the coating disposed on the luminal and /or abluminal surfaces 32a, 32b, 42a, 42b. The polymer coating 32 shown in FIG. 7B may be a drug-polymer coating or polymer coating applied by spraying, or a molten polymer applied to the brim of the hole 22 and over the marker 25'.

According to Concept C the marker can have roughened wall surfaces. FIGS. 6A and 6B show modified marker-holding strut portions 51a, 51b before and after, respectively, a marker 25' is pressed into each hole 52 of the strut portions 51a, 51b. The holes 52 are formed as bearclaw holes or holes having grooves 54 formed through the thickness and along the perimeter of the hole. The grooves 54 may be formed using a laser directed down into the hole and moved circumferentially about the perimeter to cut out the grooves 54. Each of the grooves 54 can serve as a gap that fills up with a coating or molten polymer 32 to form an adhesive binding surfaces of the marker 25' to walls of the hole 52, in the same way as the embodiments of FIGS. 4A, 4B, 5A and 5B where the binding occurs at wall corners 33, 43.

Figure 6C:
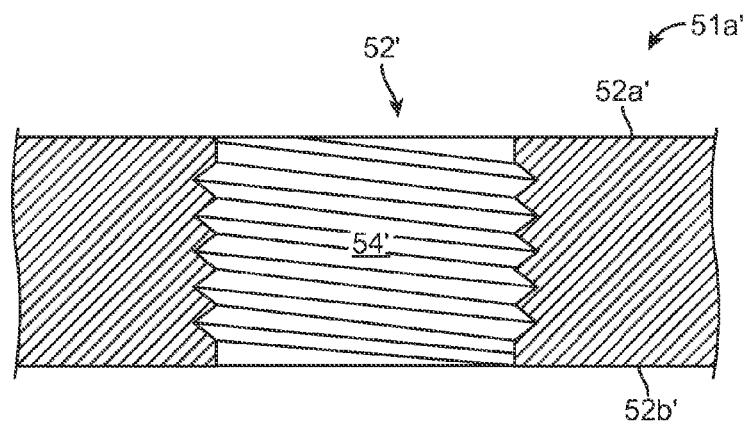
FIG. 6C is a side cross-sectional view of a link according to another embodiment.

Grooves may be formed as spiral grooves as opposed to grooves that extend straight down (i.e., into the paper in FIGS. 6A-6B). Spiral grooves may be formed by a tapping tool such as a finely threaded drill bit or screw (about 1, 2, 3, 4, 5 or 4-10 threads per 100 microns). This structure is shown in FIG. 6C where a strut portion 51a' having an abluminal surface 52a' and hole 52' is tapped to produce one or more spiral grooves surface 54'. The hole 52' may have 2 to 10 threads per 100 microns, or a groove may have a pitch of about 10, 20, 30 or 50 microns.

Any combination of the Concept B and Concept C embodiments are contemplated. A hole may be polygonal such as rectangular, square or hexagonal with the grooves formed on walls. There may be 1, 2, 3, 4, 5-10, a plurality or grooves, grooves every 10, 20, 45, or 10-30 degrees about the perimeter of the hole. "Grooves" refers to either straight grooves (FIG. 6A-6B) or spiral grooves or threading (FIG.

6C). The grooves may be formed in a polygonal hole (e.g., square, rectangular, hexagonal) or elliptical hole (e.g., a circular hole).

According to Concept D, a marker hole has a concave surface between upper and lower rims to hold a marker in place. Referring to FIGS. 8A-8B, there is shown a strut portion 61a having an abluminal and luminal surface 62a, 62b respectively and a hole 62 to receive the marker 25, as shown. The wall 64 of the hole is cylindrical, like in the FIG. 2A embodiment, except that the wall 64 includes an annular and concave surface (or groove) formed about the perimeter. The (groove) surface 64c located between the upper and lower edges of the hole 62 is between an optional upper and lower rim 64a, 64b of the hole 62. The rims 64a, 64b help retain the marker 25 in the hole 62. According to this embodiment a hole has a pseudo-mechanical interlock feature provided by the annular groove 64c. Referring to FIG. 8B the deformed marker 25' has a portion 26a generally taking the shape of the annular groove 64c having a concave shape, or displacing into the space defined by this part of the wall when the marker is forced into the hole. The rims 64a, 64b, and the convex shape of 25' nested into concave annular groove 64c, resist dislodgment of the marker 25' from the hole 62. As can be appreciated from FIG. 8B the marker 25' would have to deform before it dislodges from the hole 62. Because the marker 25' must deform to dislodge from the hole 62, the hole 62 having the annular groove 64c between upper and lower rims 64a, 64b provides a mechanical interlock. In contrast to other embodiments, the structure shown in FIG. 8B need not rely primarily or solely on friction and/or an adhesive/coating to secure the marker in place.

FIG. 8C illustrates a method for making the hole 62 according to Concept D using a laser 200 reflected off a reflective surface 204 of a reflector tool or reflector 202. The reflector 202 is frustoconical and is configured to extend up through the untapped hole 20. The reflector 202 is pressed and held against the luminal surface 62b to hold it in place. The reflective surface 204 is arranged at an angle of between 20 to 60 degrees with respect to the untapped wall of the hole 20. The surface 204 is arranged so that laser light impacts the wall 64c' at about a right angle as shown. The laser 200 is directed onto the surface 204, which reflects the light towards the wall and causes the laser energy to etch-out the groove. The laser is traced (or scanned) about the perimeter of the hole 20 to make the annular groove shown in FIG. 8A. The laser would trace a circle on the reflector 202, just inside the edges of the marker hole 20. The groove thickness (i.e., distance between the upper and lower rims 64a, 64b) can be up to about 60% to 80% and/or between about 20% to 50% of the strut thickness.

In the embodiments, the reflectors 202 having surface 204 can have a frustoconical part for each of the paired holes (FIG. 2), or instead have a set of hemispheres or cones for a set of marker holes. An alternative laser reflector would be one which does not protrude into the marker bead hole but which presents a concave surface pressed up against the bottom of the hole with edges at surface 62b. A laser beam impinging on this surface would be reflected against the opposite wall of hole 20. In another embodiment, the annular groove may instead be formed by a pin having an oblate spheroid shaped at its tip. The tip of the pin is forced into the hole 20 so that the tip sits within the hole. The hole is deformed to have an annular groove as shown in FIG. 8A. Then the marker 25 is pressed into the hole 62 to take a similar shape as in FIG. 8B.

Figure 9A:
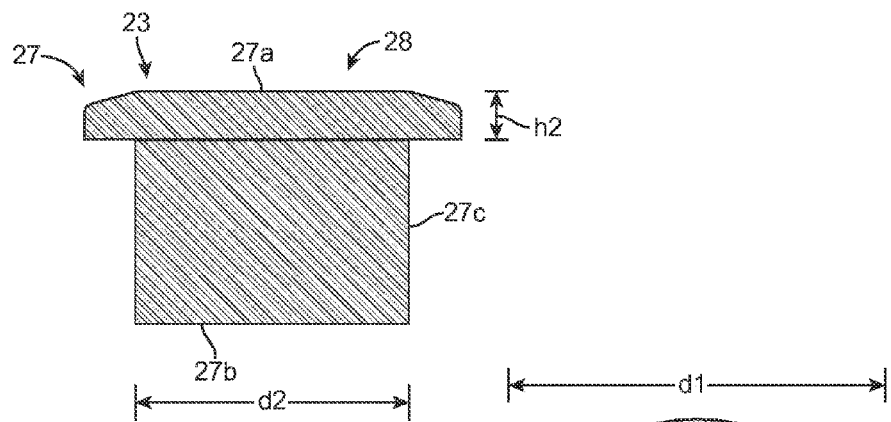
FIGS. 9A-9B show a side and top view, respectively, of a marker according to another embodiment.
Figure 9B:
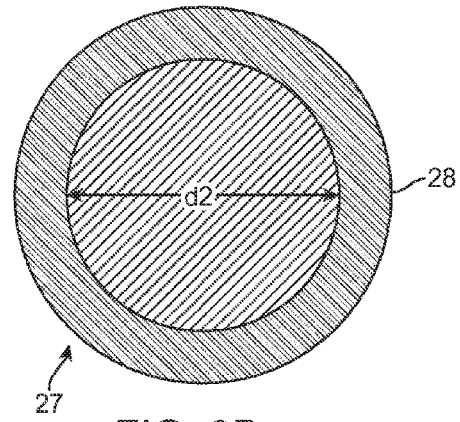

According to Concept E, a marker shaped as a rivet is used in place of the spherical marker 25. FIGS. 9A and 9B show respective side and top views of the marker 27 shaped as a rivet. The head 28 may include the abluminal surface 27a or luminal surface 27b of the rivet 27. In the drawings, the head 28 includes the abluminal surface 27a. It may be preferred to the have the head 28 be the luminal surface portion of the rivet 27 for assembly purposes, since then the scaffold may be placed over a mandrel and the tail portion of the rivet deformed by a tool (e.g., a pin) applied externally to the scaffold abluminal surface. The rivet 27 has a head diameter d1 and the shank 27c diameter d2 is about equal to the hole 22 diameter. The head 28 has a height of h2, which is about the amount the head 28 will extend beyond the abluminal surface 22a of the strut portion 21a. While not desirable, it may be an acceptable protrusion for a head 28 that does not extend more than about 25 microns, or from about 5 to 10 microns up to about 25 microns from the abluminal surface 22a, or a head that extends by an amount no more than about 25% of the strut thickness. The same extent of protrusion beyond the luminal surface 22b may be tolerated for the deformed tail of the rivet.

Figure 9C:
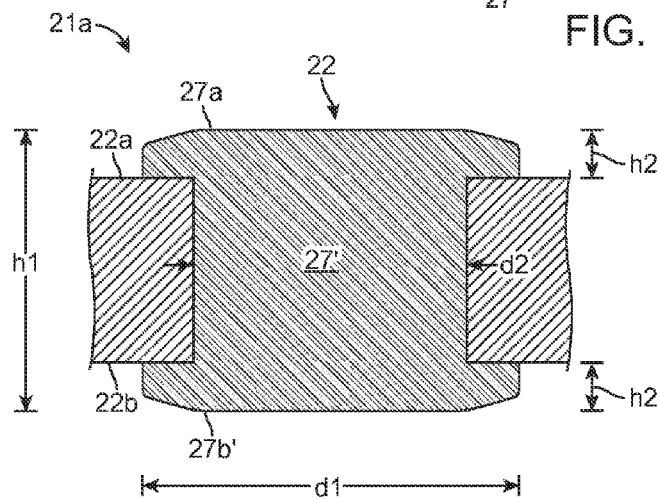
FIG. 9C is a cross-sectional view of a link having a hole and the marker of FIGS. 9A-9B embedded in the hole.

Referring to FIG. 9C there is shown the rivet in the hole 22. The deformed tail 27b' secures the rivet 27 in the hole 22. The overall height h1 is preferably not more than about 40% or about 10%-40% greater than the strut thickness (t) and the tail height is about the same as, or within 5 to 20 microns in dimension compared to the head height h2.

The rivet 27 may be attached to the hole 22 of the strut portion 21a by first inserting the rivet 27 into the hole 22 from the bore side of the scaffold so that the head 28 rests on the luminal surface 22b of the strut portion 21a. The scaffold is then slipped over a tight fitting mandrel. With the mandrel surface pressed against the head 28 a tool (e.g., a pin) is used to deform the tail 27b to produce the deformed tail 27b' in FIG. 9C. In some embodiments, the rivet 27 may be first inserted into the hole 22 from the abluminal side so that head 28 rests on the abluminal surface 22a of the strut potion 21a. With the head 28 held in place by a tool or flat surface applied against the abluminal surface, the tail 27b is deformed by a tool, pin, or mandrel which is inserted into the bore or threaded through the scaffold pattern from an adjacent position on the abluminal surface. In some embodiments the rivet 27 may be a solid body (FIG. 9A-9B) or a hollow body, e.g., the shank is a hollow tube and the opening extends through the head 28 of the rivet.

In some embodiments a rivet is a hollow or solid cylindrical tube and devoid of a pre-made head 28. In these embodiments the tube (solid or hollow) may be first fit within the hole then a pinch tool used to form the head and tail portions of the rivet.

Referring to FIGS. 10A-10B and 11A-11B there is shown embodiments for securing a marker using a starting cylindrical tube hollow (tube 65) or solid (tube 75), respectively.

Referring to FIGS. 10A-10B there is an attachment of a marker shaped as a hollow tube 65 placed into the strut portion 21a hole and deformed using a pinching tool 60. FIG. 10B shows the deformed marker 65'. The tube 65 has an inside cylindrical surface 67 and outer diameter that is about, or slightly greater than the hole 22 diameter. The tube has an undeformed length about equal to about 10%-40%, or 40%-80% greater than the strut thickness (t). The deformed tube/rivet has a deformed length (h2) of about 10-50% greater than the strut thickness and/or an undeformed length (h3) of about 15% to 70% greater than the strut thickness (t).

The pinching tool 60 includes an upper arm 60a and lower arm 60b. The deforming faces of the two arms 60a, 60b are the same. The face includes a deforming face 62*a*, 62*b* respectively shaped as an apex, point, hemisphere or convex surface, so that when pressed into the tube the end portions extending above the strut surface 22*a*, 22*b* respectively will be pushed outwardly, as shown in FIG. 10B. The arm's flattening surface 63*a*, 63*b* flattens the material against the strut surface. As can be appreciated from the drawings the deformed ends 65*a*', 65*b*' of the deformed tube 65' resemble the faces of the deforming faces 63*a*, 63*b*.

Referring to FIGS. 11A-11B there is an attachment of a marker shaped as a solid cylinder 75 placed into the strut portion 21*a* hole and deformed using a pinching tool 70. FIG. 11B shows the deformed marker 75'. The cylinder has an undeformed length about equal to about 10%-40%, or 40%-80% greater than the strut thickness (t). The deformed cylinder / rivet has a deformed length (h2) of about 10-50% greater than the strut thickness and/or an undeformed length (h3) of about 15% to 70% greater than the strut thickness (t).

The pinching tool 70 includes an upper arm 70*a* and lower arm 70*b*. The deforming faces of the two arms 70*a*, 70*b* are the same. The faces include a deforming face 72*a* for arm 70*a* and deforming face 72*b* for arm 70*b*, both of which may be shaped with an apex, point, hemisphere, or convex surface, so that when pressed into the cylinder the end portions extending above the strut surface 22*a*, 22*b* respectively will be pushed outwardly, as shown in FIG. 11 B. The arm's flattening surface 73*a*, 73*b* flattens the material against the strut surface. As can be appreciated from the drawings the deformed ends 75*a*', 75*b*' of the deformed tube 75' resemble the faces of the deforming faces 73*a*, 72*a*, 73*b*, and 73*a*.

According to additional aspects of Concept E there is a process for making radiopaque markers as rivets, mounting the rivets on a scaffold and a scaffold having such markers mounted thereon. A process for making rivet-shaped markers from beads is described first.

As discussed in connection with embodiments of a rivet marker 27 (e.g., rivet 27 and 27' depicted in FIGS. 9A, 9B and 9C) head and tail portions help to hold the marker in place, such as when an external force is applied to the rivet or the link structure is deformed during crimping or balloon expansion. In some embodiments however a tail portion, e.g., tail 27*b*' of the rivet 27' in FIG. 9C, is not present. Instead, the rivet's shank portion is deformed to be trapezoidal or frustoconical in shape or to have enlarged end (e.g., rivet 137' shown in FIG. 22A). This type of marker has been found to produce increased resistance to be being pushed out of the hole of a strut or link when the scaffold is subjected to external forces that deform the link or strut holding the marker.

It is desirable to choose the appropriate size of the bead for forming the rivet. According to some embodiments the bead size, or bead volume to use depends on the strut thickness (t), hole diameter (D2), distance between holes (D1) and rim thickness (D2) of the scaffold structure where the rivet will be mounted (e.g., the link struts having holes 22 in FIG. 14 or 15). The stock beads may be spherical, e.g., bead 25 in FIG. 2A, or cylindrical, e.g., FIGS. 10A-10B or 11A-11B. Beads made from a radiopaque material can be obtained from commercially available sources.

According to the disclosure, stock beads are used to make rivet markers for mounting in scaffold holes 22. In preferred embodiments rivet markers are mounted or engaged with scaffold holes of a strut or link having a thickness (t) that is, e.g., about 100 microns, or between 100 and 150 microns, or between 100 and 120 microns. The steps of a rivet-making process and attachment to a scaffold may be summarized as a six-step process.

STEP 1: select from the stock material a marker bead having a diameter or volume within the desired range, i.e., a diameter or volume suitable for mounting on a scaffold according to the dimensions D0, D1, D2 and t (FIG. 14). Selection of the marker bead having the desired diameter or volume, or removal of a bead too small from the lot, may be accomplished using a mesh screen. The lot of beads is sifted over a mesh screen. Beads that do not have the minimum diameter or volume will fall through openings in the mesh screen. Alternative methods known in the art may also be used to remove unwanted beads or select the right size bead.

STEP 2: deposit the bead selected from Step 1 on a die plate.

STEP 3: cold form the rivet from the bead by pressing the bead into the die plate. At temperatures close to ambient temperature force the bead through the die (e.g., using a plate, mandrel head, pin or tapered ram head) to thereby re-shape the bead into a rivet defined by the die shape and volume of the bead relative to the volume of the die receiving the bead.

STEP 4: remove the formed rivets from the die plate. The formed rivets, which can have a total length of about 190-195 microns and diameter of about 300-305 microns, are removed using a tool having a vacuum tube. The air pressure is adjusted to grip a rivet at, or release it from the tip. The rivet is removed from the die by placing the opening of the vacuum tube over the head of the rivet, reducing the air pressure within the tube to cause the head to adhere to, or become sucked into the tube tip (due to the difference in pressure) and lifting the rivet from the die.

STEP 5: while the rivet remains attached to the tip of the tube, move the rivet to a position above the hole of the scaffold, place the rivet into the hole using the same tool, then increase the air pressure within the tool to ambient air pressure. The rivet is released from the tool.

Figure 21A:
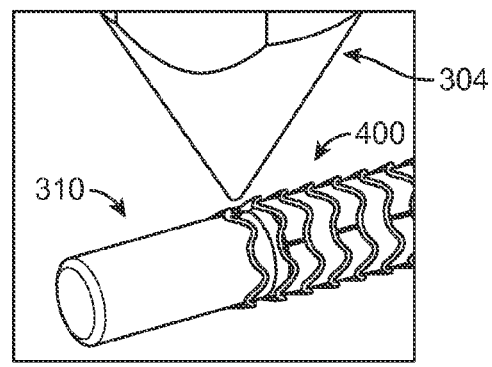
FIGS. 21A, 21B and 21C are perspective views depicting aspects of a process for deforming a rivet lodged in a scaffold hole to enhance engagement with the hole to resist dislodgment forces associated with crimping or balloon expansion.
Figure 21B:
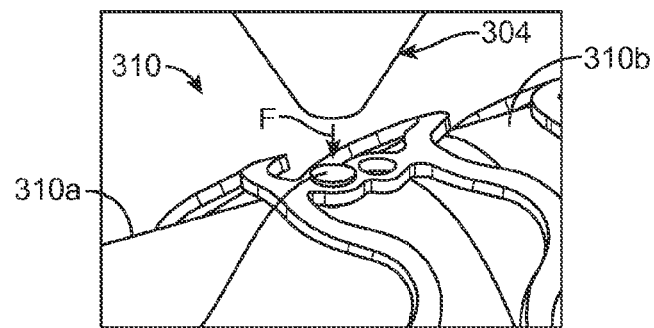
Figure 21C:
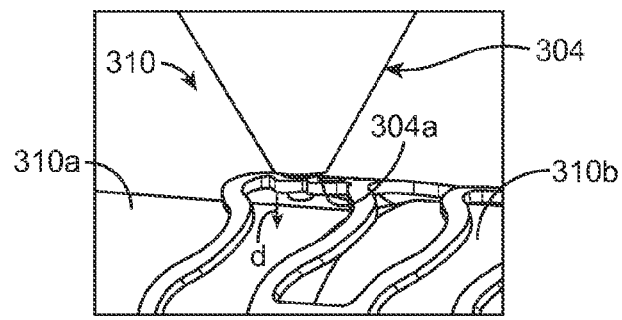

STEP 6: deform the rivet and/or hole to enhance the engagement or resistance to dislodgment of the marker from the hole., e.g., FIGS. 21A-21C.

It will be appreciated that according to STEPS 1-6 there is overcome the problem with the handling of non-spherical beads. For instance, the steps 1-6 above, wherein the rivet need not be re-orientated after being formed from a spherical bead, overcomes the problem of orientated spherical beads so that they can be aligned and placed into holes.

Figure 23A:
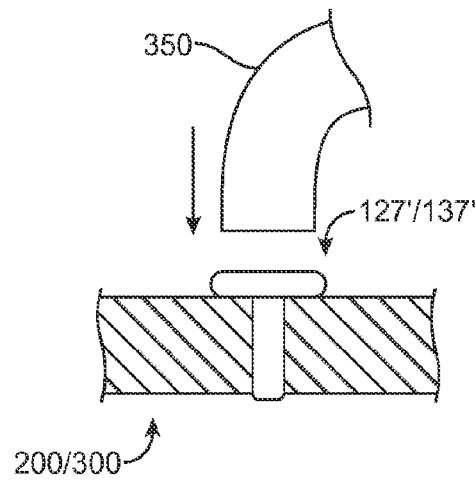
FIGS. 23A through 23C illustrate steps associated with removing a formed rivet marker from a die and placing the rivet marker into the hole of the scaffold.
Figure 23B:
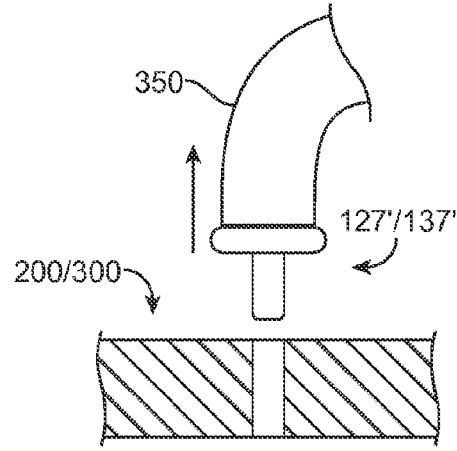
Figure 23C:
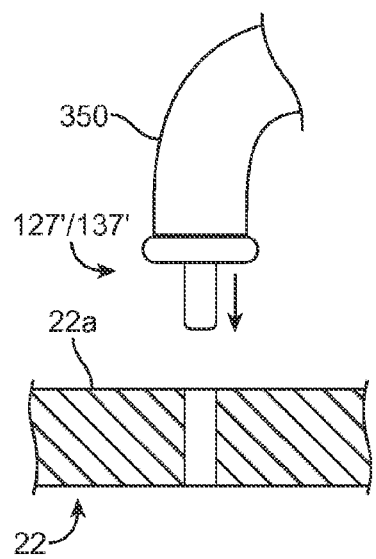

Referring to FIGS. 23A, 23B and 23C there is shown steps associated with transferring a formed rivet 127' (or 137') from a die 200 (or 300) to the scaffold strut hole 22 using a vacuum tool 350. As can be appreciated, the formed radiopaque marker 127' is extremely small, i.e., less than 1 millimeter in its largest dimension, as such the handling and orientation of the marker 127' for placement into the hole 22 is complicated (in contrast to placement of a sphere into the hole) because of the need to orient the shank properly with respect to the hole. For this reason the swaging or forging process is combined with placing into the scaffold hole, by removing the rivet 127' from the hole 200 with the tool 350, FIG. 23A, maintaining the orientation by keeping the rivet 127' attached to the tool, FIGS. 23B-23C, and then placing the rivet 127' into the hole 22*a*, FIG. 23C.

Figure 17:
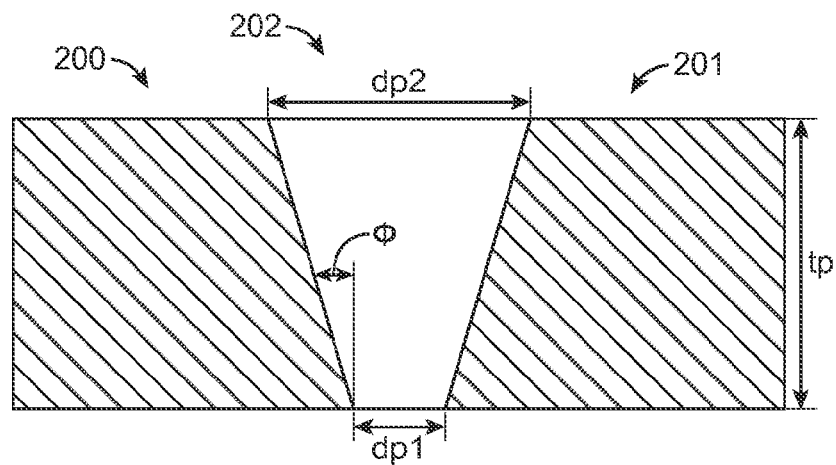
FIG. 17 is a side-cross section of a first die for forming a rivet marker from a radiopaque bead.
Figure 18A:
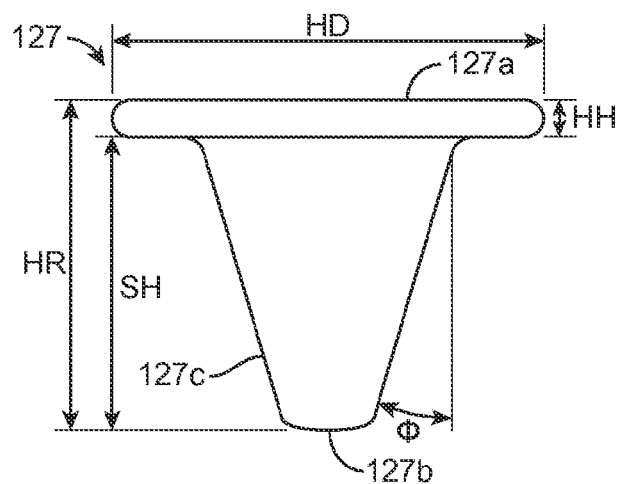
FIG. 18A is a side view of a rivet marker formed using the die of FIG. 17.

With reference to FIGS. 17 and 18A there is shown a first embodiment of a die 200 and marker 127 formed using the die 200, respectively, according to the disclosure. The die is a flat plate having a top surface 201 and a through hole extending from an upper end 201 to a lower end. The hole has an upper end diameter dp2 and lower end diameter dp1 less than dp2. The hole 202 is preferably circular throughout, although in other embodiments the hole may be rectangular or hexagonal over the thickness tp, in which case dp1 and dp2 are lengths or extents across the hole (as opposed to diameters). And the plate 200 has a height tp. The taper angle is related to dp2 and dp1 by the expression $\tan \Phi = (\frac{1}{2}(dp2-dp1)/tp)$, which in a preferred embodiment $\Phi$ is 1 to 5 degrees, 5-10 degrees, 3-5, or 2-4 degrees. The shape of die 200 produces a frustoconical shank, as depicted in FIG. 18A. A stock bead (not shown) is placed on the upper end of the opening 202 so that the bead sits partially within the hole 202. A flat plate, mandrel or pin ("ram head") is then pressed into the top of the bead so that the bead is forced into the hole 202. The bead is forced into the hole until the ram head is about distance HH from the surface 201. The rivet 127 formed from the foregoing forming process has the taper angle $\Phi$ over all of, or a substantial portion of the shank height SH and the shank shape is frustoconical. The overall rivet height is HR, the head thickness is HH and the head diameter is HD. In some embodiments the angle $\Phi$ may be sufficiently small so that the shank may be treated as a cylinder, or $\Phi$ is about zero.

Figure 19:
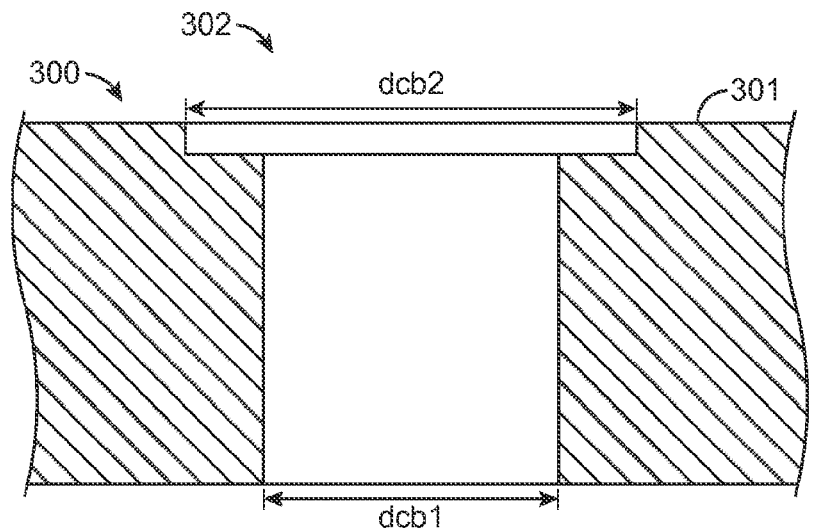
FIG. 19 is a side-cross section of a second die for forming a rivet marker from a radiopaque bead.
Figure 20A:
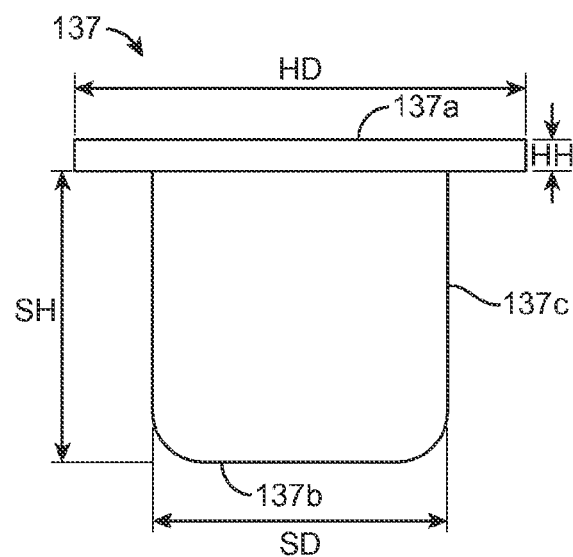
FIG. 20A is a side view of a rivet marker formed using the die of FIG. 19.

With reference to FIGS. 19 and 20A there is shown a second embodiment of a die 300 and marker 137 formed using the die 300, respectively, according to the disclosure. The die is a flat plate having a top surface 301 and a hole extending from an upper end 301 to a lower end. The hole has a constant diameter dcb1 throughout. A counter bore is formed on the upper end 301. The counter bore diameter is dcb2. The hole 302 is preferably circular throughout, although in other embodiments the hole 302 may be rectangular or hexagonal, in which case dcb1 is a length or extent across the hole (as opposed to a diameter). The shape of die 300 produces a rivet having a stepped cylindrical shape or cylindrical shank with a head, as depicted in FIG. 20A. A stock bead (not shown) is placed on the upper end of the opening 302 so that the bead sits partially within the hole 302. A ram head is then pressed into the top of the bead so that the bead is forced into the hole 302. The bead is forced into the hole until the ram head is about distance HH from the surface 301. The rivet 137 formed from the foregoing forming process takes the shape shown in FIG. 20A. The overall rivet height is SH+HH, the head thickness is HH, the shank height is SH and the head diameter is HD.

TABLES 2 and 3, below, provide examples of rivet dimensions for a rivet intended for being secured within a link hole 22 such as shown in FIG. 15. In this example the thickness of the link is 100 microns and the values in microns (μm) for D0, D1 and D2 are 241, 64 and 64, respectively.

Values for the die 200 dimensions tp, dp2 and dp1 are 178, 229 and 183. The resulting formed rivet dimensions using die 200 are shown in TABLE 2. As can be appreciated from the results, the shank length (or height) is more than 150% of the link thickness and the rivet head diameter (HD) is significantly larger than the hole 22 diameter. The lower portion of the shank is relied on to form a tail portion of the rivet. The mean and standard deviation for HD, SD, and SL are based on the respective "n" samples of rivets measured.

TABLE 2

Rivet formation using tapered plate (FIG. 18A)

| | | inches | microns | n |
|---|---|---|---|---|
| Rivet head diameter (HD) from taper plate | mean | 0.0123 | 312 | 51 |
| | standard deviation | 0.0015 | 38 | |
| O.D. Rivet head diameter post swage | mean | 0.0132 | 335 | 27 |
| | standard deviation | 0.0011 | 28 | |
| Shank Diameter (SD) | mean | 0.0089 | 226 | 51 |
| | standard deviation | 0.0004 | 10 | |
| Shank Length (SL) | mean | 0.0072 | 183 | 37 |
| | standard deviation | 0.0009 | 23 | |

Values for the die 300 dimensions dcb2 and dcb1 are 305 and 203. The resulting formed rivet dimensions using die 300 are shown in TABLE 3. The mean and standard deviation for HD, SD, HH and SL are based on the respective "n" samples of rivets measured.

TABLE 3

Rivet formation using counter bore plate (FIG. 20A)

| | | inches | microns | n |
|---|---|---|---|---|
| Rivet head diameter (HD) from Die | mean | 0.012 | 305 | 19 |
| | standard deviation | 0.0003 | 10 | |
| O.D. Rivet head diameter post swage | mean | 0.013 | 330 | 30 |
| | standard deviation | 0.0007 | 18 | |
| Rivet head height (HH) | mean | 0.001 | 25 | 31 |
| Shank Diameter (SD) | standard deviation | 0.008 | 203 | 31 |
| Shank Length (SL) | mean | 0.0075 | 190 | 24 |
| | standard deviation | 0.0008 | 20 | |

In TABLES 2 and 3 "O.D. Rivet head diameter post-swage" refers to the outer diameter of the rivet marker head after the rivet marker is pressed into the scaffold hole.

Discussed now are examples of processes for mounting either of the rivets 127, 137 to the scaffold hole 22. According to some embodiments the rivet shank is placed into the hole 22 from the abluminal or outer side of the scaffold, so that the head sits on the abluminal surface 22a. The rivet may instead be placed from the luminal side of the hole. The rivet is firmly pressed into the hole so that a maximum portion of the shank extends from the luminal or abluminal sides, respectively.

Figure 18B:
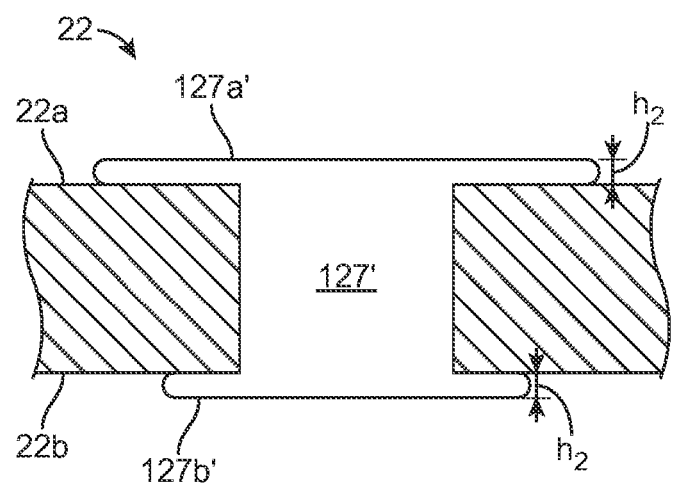
FIG. 18B is a side cross-section of a scaffold strut with the marker of FIG. 18A engaged with a hole of the strut and after a forming process deforms the marker to make upper and lower rims retaining the marker in the hole.

For the rivet 127 after it is placed in the hole 22 the side opposite the head is subjected to a swaging process. With reference to FIG. 18B there is shown in cross-section the deformed rivet 127' in the hole 22. The rivet 127' has a head 127a' that extends from the surface 22a by an amount h2. The length h2 may be about 25 microns, between 25 and 50 microns or between 5 and 50 microns. The same dimensions apply to a tail 127b' that extends from the opposite surface of the link (e.g., luminal surface). The diameter of the head 127a' can be larger than the tail, or the tail 127b' diameter can be larger than the head 127a' diameter. The tail portion is formed from the extended shank length that protrudes from the link surface by swaging. The tail 127b' is formed by swaging. For example, the rivet 127 is placed in from surface 22a (abluminal side) so that a significant portion of the shank length, e.g., 50% of the strut thickness, extends from the luminal side. A cylindrical mandrel (not shown) is placed through the scaffold's bore. This mandrel has an outer diameter slightly less than an inner diameter of the scaffold and provides a swaging surface to form the tail 127b'. The mandrel is rolled back and forth over shank portion extending form the luminal surface. This motion causes the shank material to flatten out around the hole, thereby producing the tail portion 127b'. The resulting rivet 127' is secured in place, at least in part, by the tail portion 127b' resisting forces tending to push the rivet towards the abluminal side of the hole and the head portion 127a' resisting forces tending to push the rivet towards the luminal side of the hole 22. As shown, the deformation of the shank produces the tail 127b' having a flange disposed on the surface 22b. The flange may be circular like the head and may have a flange radial length greater or less than the radial length of the flange of the head 127a'.

Figure 22A:
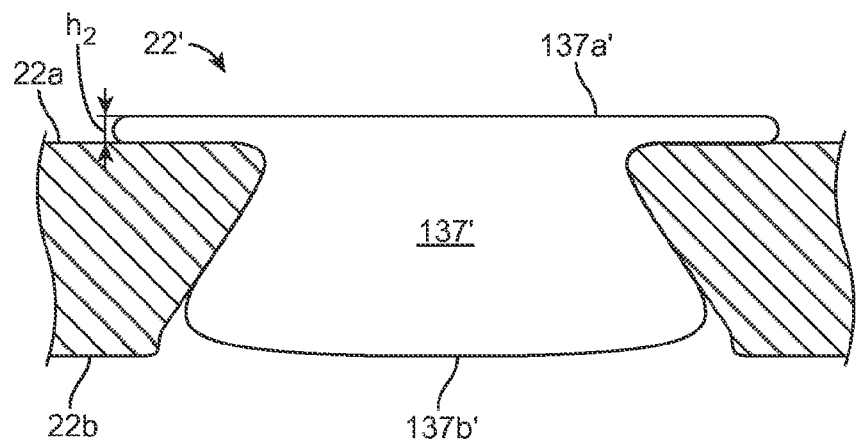
FIG. 22A is a side cross-sectional view of a deformed rivet marker and scaffold hole following the process described in connection with FIGS. 21A-21C.
Figure 22B:
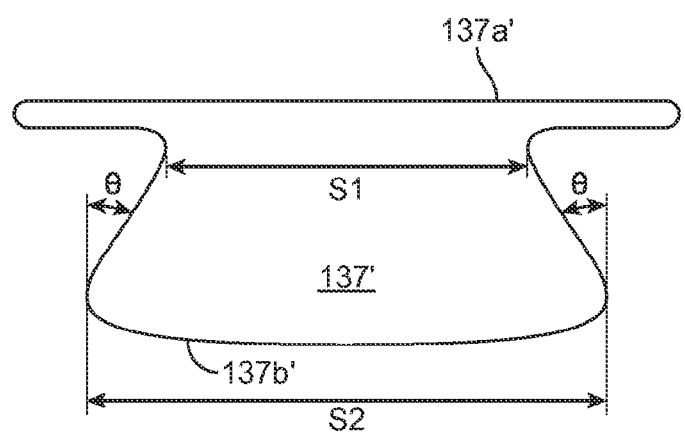
FIG. 22B is a view of the deformed marker illustrated in FIG. 22B.

With reference to FIGS. 22A and 22B, a stepped mandrel is used in conjunction with a ram head to produce the rivet 137' from rivet 137. The rivet has a shank 137' that is reformed from, e.g., a generally-cylindrical shape when using the die 300, FIG. 19, to the shape shown in FIGS. 22A through 22C. This shank shape may be characterized by a taper angle $\ominus$ of magnitude of from between about 5 and 15 degrees, 5 to 9 degrees, or about 3 to 8 degrees. The shank according to some embodiments of a rivet in the hole 22 is frustoconical in shape, wherein the shank end opposite, or distal of the head 137a', or end 137b' is larger or has a larger diameter than the shank portion proximal or nearest the head 137a'. The deformed shank 22' may have a shank diameter S2 nearest one of the abluminal and luminal side openings of the hole 22' that is larger than the shank diameter S1 nearest the other of the luminal and abluminal side opening, or S2>S1. According to some embodiments, as shown in FIG. 22A the cylindrical hole 22 is also deformed into the hole 22' that has an opening at surface 22b larger than the hole opening at surface 22a. According to some embodiments both the hole 22 and rivet 137 are deformed when the rivet 137 is mounted on the scaffold.

The structure illustrated in FIG. 22A may be made by a second process of attaching a rivet marker to a scaffold hole 22. In contrast to the first process a tool is not rolled across the surface where the shank tail portion protrudes from the hole opening. Instead, the shank tail end is pushed directly into a non-compliant surface, which can be a surface of a metal mandrel. The rivet is forced to deform by a compression force between the surface of the mandrel and head of a ram 304, which pushes the rivet into the mandrel surface. The first process producing the deformed rivet 127' by contrast is formed by a combination of rolling a hard surface into the shank and a restraint on the head 127a, which holds the rivet head against the surface 22a while the tail end 127b is being swaged. Under the second process the force line of action is completely along the axis of the rivet, or perpendicular to the rivet head. The result is a flattened or widened shank portion and deformed hole with little or no flange or rim formed from the tail portion of the shank.

The second process is now described in further detail with reference to FIGS. 21A-21C. The scaffold 400 is placed over a stepped mandrel 310. This mandrel has a first outer diameter and a second outer diameter, which is less than the first outer diameter. The scaffold portion holding the marker 137 is placed over the lower diameter portion of the mandrel 310. The larger diameter portion of the mandrel 310 holds the adjacent parts of the scaffold. The lower diameter part of the mandrel 310 has a surface 310a and the larger diameter portion has a surface 310b. As shown in FIGS. 21B, 21C the ram 304 pushes with a force F (FIG. 21B) the scaffold portion holding marker 137 into the mandrel surface 310a, which causes this scaffold end to deflect a distance "d" towards the surface 310a (FIG. 21A). After the scaffold reaches the surface 310a, the ram 304 continues to push into the scaffold portion holding the marker (by pressing directly against the head 137a) to create the deformed marker 137' and hole 22' as shown in FIG. 22A. The surface 310a chosen may be smooth or free of grooves, pitting, depressions or other surface irregularities (other than a surface of a cylinder) that would inhibit flow of material during swaging. In a preferred embodiment the mandrel surface is smooth compared to the surface of the head 304 pressed into the rivet marker 137. That is, the coefficient of friction (Mu) between the head 304 and surface 137a' is greater than Mu between surface 310a of mandrel 310 and surface 137b'.

The shape of the deformed shank 137' and hole 22' shown in FIG. 22b produced higher push-out forces than previously believed (a "push-out force" means the force needed to dislodge the marker from the hole). Indeed, unexpectedly it was discovered that the deformed rivet 137' and hole 22' had a higher resistance to dislodgement than a marker fit into a link having an over 50% higher thickness, irrespective of the presence of the head 137a'. For example, tests for a minimum dislodgment force needed to push the rivet 137' out from the side 22a of the hole 22' of a strut having a 100 micron thickness were higher than the dislodgment force needed to push out a marker mounted according to US20070156230 (FIGS. 8A, 8B or where the sphere is deformed more into a cylinder when in the depot, thus increasing the surface-to-surface contact to a maximum) and for a hole of a strut having an about 50%-higher thickness (158 microns vs. 100 microns). As TABLE 4 demonstrates:

TABLE 4

| Scaffold (TABLE 1) | Marker process | Bead volume ($\mu m^3 \times 10^6$) | US20070156230 (FIGS. 8A, 8B) | Interior hole surface area (thickness × diameter × π) ($\mu m^2 \times 10^3$) | Push-out force (gram-force) from luminal to abluminal side of link |
|---|---|---|---|---|---|
| A | Press sphere into hole (US20070156230, FIGS. 8A, 8B) | 6.76 | wall thickness 158 μm and hole diameter 234 μm | 116.2 | 51.5 (n = 8) |
| B | FIGS. 21A-21C and using rivet marker 137 | 6.76 | wall thickness 100 μm and hole diameter 241 μm | 75.7 | 78.6 (n = 31) |

There are higher push-out forces for scaffold B, even though scaffold A has more surface area for contact with the marker, thus higher frictional forces resisting dislodgment. This result indicates that the deformation that occurs during the swaging process resulting in the deformed rivet marker and hole of FIG. 22A has a significant effect on the push-out force (note: the gram-force push-out force reported in TABLE 4 was applied to the luminal side 22b for scaffold B). Given the more than 50% higher wall thickness Scaffold A should have had a higher dislodgment force (the same bead material, bead volume and poly(L-lactide) scaffold material for Scaffold A and B). The higher dislodgment force can be explained by the shape of the deformed shank and hole, which essentially produces a lower portion 137b' that is significantly larger than the opening 22a of the strut 22. Thus, the dislodgment force must be high enough to deform the opening 22a' and/or shank portion 137b' in order to dislodge the marker from the 22a side of hole 22' (as opposed to only needing to overcome essentially a frictional force between the material and walls of the hole).

The shape 137' in FIG. 22B may be formed by a swaging process that deforms the rivet while it sits inside the hole 22. The rivet may have the shape and/or characteristics of rivet 27, 127 or 137 before swaging. The flow of rivet material transversely (shear flow) during swaging near tail portion 137b' causes it to expand out and also yield (enlarge) the strut hole nearer to opening 22b'. This produces the trapezoidal-like or frustoconical shape of the rivet shank and hole. The swaging process of FIGS. 21A-21C applies equal and opposite forces that are about co-linear with the axis of symmetry of the rivet (as opposed to a rolling motion on one side). If instead a cylinder or sphere (as opposed to a rivet) were placed in the hole 22 and about the same coefficient of friction (COF) existed between the swaging surface 310a and tail 137b as the COF between the swaging surface 304 and the head 137a, but otherwise the same swaging process as in FIGS. 21A-21C, it is believed that the result would be a more symmetric deformed marker, e.g., a squashed cylinder or barrel-shaped marker depending on the COF, such as the shape shown in US20070156230. This result can be appreciated from Kajtoch, J *Strain in the Upsetting Process*, Metallurgy and Foundry Engineering, Vol. 33, 2007, No. 1 (discussing influence of coefficient of friction between ram and ingot on resulting shapes for slenderness ratios greater than 2). The shape of the radiopaque material forced into the hole is also a factor, e.g., a rivet 137 verses a sphere (scaffold A). The presence of the head on one side results in a shank forming an asymmetric shape about the strut mid-plane axis. It is believed that a combination of the rivet shape and coefficient of friction differences produced the favorable result.

In a preferred embodiment a smooth mandrel 310 surface 310a presses against the surface 137b, as compared to a more rough surface of the head 304 that presses against the surface 137a. In a preferred embodiment the coefficient of friction for the abluminal side was greater than 0.17 or Mu>0.17, whereas the coefficient of friction on the luminal side was less than 0.17 or Mu<0.17. As discussed above, the effect of a difference in the coefficient of friction can be explained by the restraint on shear or later material flow near the end abutting the respective swaging head. If the coefficient of friction is sufficiently low then the surface area expands out laterally, as opposed to being held relatively constant. Thus, since Mu is less on the luminal side there is more lateral flow than on the abluminal side. The result, when combined with use the rivet shape, is believed to be the frustoconical shape as disclosed, e.g., as shown in FIGS. 22A-22B, which may be thought of as a shank having a locking angle $\ominus$.

Figure 16:
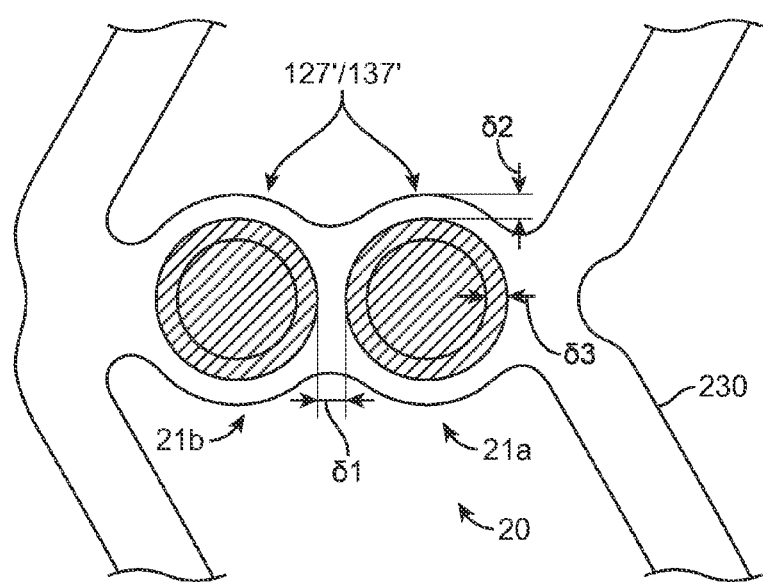
FIG. 16 is a side view profile of the scaffold structure form FIG. 15 with a pair of markers engaged with holes of the scaffold.

With reference to FIG. 16, the rivet 127'/137' may be inspected after placed to evaluate its capacity for resulting forces that tend to dislodge the rivet 127'/137' from the hole 22. These dislodging forces can be produced by a pressurized balloon surface or a deformation of nearby scaffold structure tending to deform the hole 22, such as when the scaffold is crimped or balloon expanded. According to one aspect, the rivet heads and/or tails of the rivet 127'/137' pair may be inspected to determine whether the minimum distances $\delta1$, $\delta2$, and $\delta3$ (FIG. 16) are satisfied. The distances $\delta1$, $\delta2$, and $\delta3$ reflect either or both a minimum size of the head 127a' and/or tail 127b', which indicates both that the rivet should hold in the hole 22 (if the head or tail is too small in diameter it cannot resist as well the dislodging forces) and that excess rivet material will not cause problems such as balloon puncture or vessel irritation when the scaffold is implanted within a vessel. According to the embodiments the minimum distance from the end of the marker head/tail to the brim of the strut (or link) portion 21a/21b, $\delta2$ that is, can be about 10%, 25% and up to 50% of D2. Above 50% means the head or tail can be too small to hold the rivet in place. For a head/tail equal to, or greater than D2 the head may or does extend beyond the brim of the strut/link, which can lead to problems such as forming a relatively sharp edge than can damage the balloon or irritate adjacent tissue. The minimum distance between the marker heads / tails, $\delta1$ that is, is 0 or up to 25% of the distance D1. If the rims or heads of the markers overlap each other this can exceed the maximum height desired for the strut (about 160 microns). The minimum length for the head/tail extending to the right or left of the hole 22, $\delta3$ that is, is anything greater than 50% of D2.

According to Concept F, an irregular-shaped marker having protruding edges is placed in a lased hole prior to a thermal process that shrinks the lased hole. Polymeric bioresorbable scaffolds may be laser cut from a tube. This thin wall, precision tubing can be fabricated by extrusion and expansion processes that include stretch blow molding. The tubing resulting from such processes is formed by deformation of the polymer, which can result in residual stresses remaining in the tube. Heating the tube above its glass transition temperature (Tg) releases these stresses and can be used advantageously to shrink features such as lased marker bead holes to increase securement of a previously placed radiopaque marker. In an alternative embodiment, the temperature of the scaffold is raised above the Tg of the tube material and the marker placed into the softer, heated polymer. This allows the polymer to become more compliant, or flow and thus allow a marker, particularly an irregularly shaped marker, to interact with the polymer surfaces to a greater degree, thereby raising the frictional forces and/or forming a mechanical fit, depending on the marker type used.

Referring to FIG. 12A and 12B there is shown an irregularly shaped marker 85 placed in the hole 22 of the strut portion 21a. The hole 22 may be at ambient temperature or at an elevated temperature (about 0-20 Degrees C above the Tg of the strut material). Alternately, the hole 22 is heated above the Tg after the marker is inserted. The marker 85 has bumps, edges, corners or burrs 81 over its surface that when placed in the hole 22 deforms the hole, as illustrated in FIG. 12B. The engagement between the marker 85 and hole may form a mechanical interlock. For a marker with cylindrical symmetry, a degree of roughness can be defined as the maximum and minimum distances in terms of radius from the markers cylindrical axis (e.g., difference between inner and outer diameter as a maximum degree of roughness, or % of inner or outer diameter). For the marker 85 this distance from max to min may be between 5 to 50% of the maximum marker diameter. The marker may have a flower, star or polygonal shape to produce the same effect. When placed in the hole 22 the hole 22 deforms. The marker 85 may or may not deform, depending on the temperature of hole 22 and the hardness of the marker material.

According to another aspect of the disclosure there is a heating step for a scaffold following marker placement. In some embodiments this heating step may correspond to a rejuvenation step of the scaffold polymer, prior to crimping, to remove aging effects of the polymer.

Thermal rejuvenation (including thermal treatment of a bioresorbable scaffold above Tg, but below melting temperature (Tm) of the polymer scaffold) prior to a crimping process may reverse or remove the physical ageing of a polymeric scaffold, which may reduce crimping damage (e.g., at the crests of a scaffold) and/or instances of dislodgment of a marker.

According to some embodiments a scaffold is thermally treated, mechanically strained, or solvent treated to induce a rejuvenation or erasure of ageing in a polymer shortly before crimping the scaffold to a balloon and after marker placement. Rejuvenation erases or reverses changes in physical properties caused by physical ageing by returning the polymer to a less aged or even an un-aged state. Physical ageing causes the polymer to move toward a thermodynamic equilibrium state, while rejuvenation moves the material away from thermodynamic equilibrium. Therefore, rejuvenation may modify properties of a polymer in a direction opposite to that caused by physical ageing. For example, rejuvenation may decrease density (increase specific volume) of the polymer, increase elongation at break of the polymer, decrease modulus of the polymer, increase enthalpy, or any combination thereof.

According to some embodiments, rejuvenation is desired for reversal or erasure of physical ageing of a polymer that was previously processed. Rejuvenation is not however intended to remove, reverse, or erase memory of previous processing steps. Therefore, rejuvenation also does not educate or impart memory to a scaffold or tube. Memory may refer to transient polymer chain structure and transient polymer properties provided by previous processing steps. This includes processing steps that radially strengthen a tube from which a scaffold is formed by inducing a biaxial orientation of polymer chains in the tube as described herein.

In reference to a marker—scaffold integrity or resistance to dislodgment during crimping, it has been found that a heating step can help reduce instances where crimping causes dislodgment of a marker. According to some embodiments, any of the foregoing embodiments for a marker held within the scaffold hole 22 can include, after the marker has been placed in the hole, a heating step shortly before crimping, e.g., within 24 hours of crimping. It has been found that the scaffold is better able to retain the marker in the hole 22 following heating. A mechanical strain, e.g. a limited radial expansion, or thermal rejuvenation (raise the scaffold temperature above the glass transition temperature (Tg) of the load-bearing portion of the scaffold polymer for a brief time period) can have a beneficial effect on scaffold structural integrity following crimping and/or after balloon expansion from a crimped state.

In particular, these strain-inducing processes tend to beneficially affect the hole 22 dimensions surrounding the marker when the hole is deformed in the manner discussed earlier in connection with FIGS. 22A-22b.

According to some embodiments the scaffold after marker placement is heated to about 20 degrees, or 30 degrees above the glass transition temperature of the polymer for a period of between 10-20 minutes; more preferably the scaffold load bearing structure (e.g., the portion made from a polymer tube or sheet of material) is a polymer comprising poly(L-lactide) and its temperature is raised to between about 80 and 85 Deg. C for 10-20 minutes following marker placement.

Figure 22C:
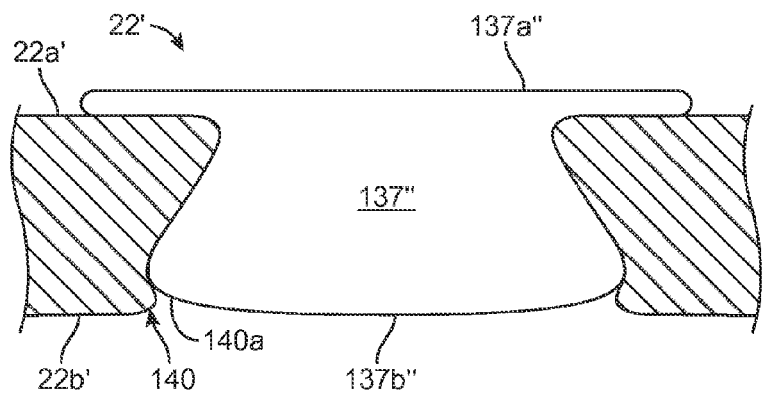
FIG. 22C is a side cross-sectional view of the rivet and marker hole from FIG. 22A following a heating step.

According to some embodiments it has been found that raising the temperature of the scaffold after marker placement re-shaped portions of the hole 22 to improve the fit of the marker in the hole. With reference to FIG. 22C after the rivet marker 137 is placed in the hole 22 according to the second process the hole shape deforms to produce a lip or edge 140 at the end 137b'', which may produce a higher resistance to dislodgment than for a scaffold-marker structure not subsequently treated by a rejuvenation step. The surface 140a of the lip 140 interferes more with dislodgment of the marker when a force is directed towards the end 22b'.

According to Concept G, a snap-in marker is used. Referring to FIGS. 13A and 13B there is shown a marker 95 having a preformed head 98 and tail 92. The shank 95c of the marker has an extent about equal to that the hole 22, which in this case is a diameter. The length of the shank is about, slightly less, or slightly more than the strut thickness. In other embodiments the marker 95 may be rectangular, hexagonal or polygonal for fitting into the holes shown in FIGS. 4A, 5A, 6A or 6C. The distance between abluminal surface 95a and luminal surface 95b in FIG. 13B satisfies inequality IE.2 or IE.4, defined below.

Platinum, and especially platinum/iridium alloys, are stronger than polymeric materials because they are metals. Many assembly and securement process use snap-fit parts where the tolerances and shapes are designed to hold parts together without fasteners. The main feature of the marker 95 is the head 98 and tail 92 having an enlarged diameter over the shank 95c part. There could be formed on portions 98 and 92 round ridges, or more wedge shaped features. When pressed in, the polymer will deform preferentially allowing the tail 92 or head 98 to pass through, or imbed within the hole to become partially or fully recessed within the hole 22. When the tail 92 or head 98 passes completely through hole 22, the polymer surface 22a or 22b will snap under marker feature 98 or 92, securing it and preventing movement in either direction.

With respect to any of Concepts A through G, the marker material may be platinum, platinum/iridium alloy, iridium, tantalum, palladium, tungsten, niobium, zirconium, or alloys thereof. The marker material may also be of biodegradable metals such as iron, zinc, magnesium, manganese or their alloys.

For some embodiments included under Concept A (e.g., the embodiments shown in FIGS. 3A-3C); some embodiments included under Concept E (e.g., the embodiments shown in FIGS. 9A-9C, 10A-10B and 11A-11B); and some embodiments included under Concept G (e.g., the embodiments shown in FIGS. 13A-13B) the following inequalities IE.1-IE.4 apply:

$$t \times (1.2) \leq L \leq t \times (1.8) \text{ or } 1.2 \leq (L/t) \leq 1.8 \qquad \text{IE.1}$$

$$t \times (1.1) \leq L' \leq t \times (1.5) \text{ or } 1.1 \leq (L'/t) \leq 1.5 \qquad \text{IE.2}$$

$$t \times (1.0) \leq L \leq t \times (1.8) \text{ or } 1.0 \leq (L/t) \leq 1.8 \qquad \text{IE.3}$$

$$t \times (1.0) \leq L' \leq t \times (1.5) \text{ or } 1.0 \leq (L'/t) \leq 1.5 \qquad \text{IE.4}$$

Where:
t is the average strut, bar arm or link thickness, or wall thickness of the tube from which the scaffold was made. The thickness t may vary between about 80 to 150 microns, 80 to 120 microns, 80 to 110 microns, 80 to 100 microns, or the thickness may be about 100 microns, or the thickness may be up to 130 or 140 microns;

L is an undeformed length of the marker (Concept E); and

L' is a deformed length of the marker (measured from the abluminal surface portion to the luminal surface portion for Concept E), length of the marker (Concept G), or distance between abluminal and luminal surfaces of a coating and/or polymer fill (Concept A).

Exemplary values for t are about 80 microns to 120 microns, or about 100 microns and L' or L being between about 100 microns and 150 microns.

The relations IE.1, IE.2, IE.3 and IE.4 reflect a need to maintain a low profile for struts exposed in the bloodstream, while ensuring the marker will be securely held in the strut. The concern addressed here is the degree thrombogenicity of the scaffold, which can be influenced by a strut thickness overall and/or protrusion from a strut surface. Blood compatibility, also known as hemocompatibility or thromboresistance, is a desired property for scaffolds and stents. The adverse event of scaffold thrombosis, while a very low frequency event, carries with it a high incidence of morbidity and mortality. To mitigate the risk of thrombosis, dual anti-platelet therapy is administered with all coronary scaffold and stent implantation. This is to reduce thrombus formation due to the procedure, vessel injury, and the implant itself. Scaffolds and stents are foreign bodies and they all have some degree of thrombogenicity. The thrombogenicity of a scaffold refers to its propensity to form thrombus and this is due to several factors, including strut thickness, strut width, strut shape, total scaffold surface area, scaffold pattern, scaffold length, scaffold diameter, surface roughness and surface chemistry. Some of these factors are interrelated. The effect of strut thickness on acute thrombogenicity has been documented and studied both in vivo and in silico.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A method for making a medical device, comprising:
    using a polymer scaffold including a strut having a hole formed in the strut, wherein the strut has a thickness of between 80 and 120 microns measured between a first side of the strut and a second side of the strut and the strut comprises poly(L-lactide); and
    using a radiopaque rivet marker having a head and a shank; and
    placing the rivet into the hole so that the head is disposed on a first surface of the first side of the strut; and
    swaging the rivet including making a deformed shank from the shank while the rivet sits in the hole;
    wherein the head resists a first push-out force acting on the first surface by the head interfering with the first side of the hole;
    wherein the deformed shank resists a second push-out force acting on a second surface of the second side of the strut by the deformed shank interfering with the second side of the hole; and
    wherein before the swaging the hole is a cylindrical hole and after the swaging the hole is a tapered hole.

2. The method of claim 1, wherein
    the first surface is one of a luminal and abluminal surface of the scaffold and the second surface is the other one of the luminal and abluminal surface,
    the strut has a width, and
    a ratio of the width to the thickness is between 1.2 and 2.0.

3. The method of claim 1, wherein the swaging includes compressing the shank between a ram head and a mandrel, wherein a surface of the ram head has a higher coefficient of friction (Mu) than a Mu for a surface of the mandrel.

4. The method of claim 1,
    wherein the shank has a shank length greater than the strut thickness,
    wherein the shank is a cylinder, and
    wherein the deformed shank is a frustum.

5. The method of claim 4,
    wherein the head is disposed at a first opening of the first side of the hole and a base of the frustum is disposed at a second opening of the second side of the hole, and
    wherein the swaging makes the second opening larger than the first opening.

6. The method of claim 1, wherein the deformed shank has a first end proximal of the head and a second end distal of the head, the first end is disposed at a first opening of the hole and the second end is disposed at a second opening of the hole,
    wherein prior to the swaging the first and second ends have the same diameter, and
    wherein the swaging deforms the second opening and the second end such that the second end and second opening are larger than the first end and the first opening, respectively.

7. The method of claim 1, wherein the marker rivet has an undeformed length (L) before the swaging, a deformed length (L') after the swaging, and L, L' and the strut thickness (t) are related by $$t\times(1.2)\le L\le t\times(1.8) \text{ and } 1.2\le (L/t)\le 1.8; \text{ and}$$

$$t\times(1.1)\le L'\le t\times(1.5) \text{ and } 1.1\le (L'/t)\le 1.5.$$

8. The method of claim 1, wherein the scaffold strut comprises poly(L-lactide).

9. The method of claim 1, wherein the scaffold is made from a polymer having a glass transition temperature (Tg), and wherein the scaffold is heated to a temperature of 0-20 degrees Celsius above its Tg after the rivet is deformed.

10. The method of claim 1, wherein the rivet is comprised of platinum, platinum/iridium alloy, iridium, tantalum, palladium, tungsten, niobium, zirconium, iron, zinc, magnesium, manganese or their alloys.

11. The method of claim 1, wherein the rivet is placed into the hole using a tool, and the tool comprises a vacuum tip configured for grabbing the head of the rivet and releasing the head therefrom by modifying a gas pressure at the tip.

12. The method of claim 1, wherein the first push-out force or the second push-out force is about an 80 gram-force.

13. A process for attaching a radiopaque material to a polymeric scaffold, comprising:
    using a die, deforming a spherical bead into a rivet having a head and shank, the bead comprising the radiopaque material;
    attaching a tool to the rivet head, including creating a pressure difference at a tip of the tool to adhere the rivet head to the tool tip thereby, enabling the tool to lift and remove the rivet from the die and maintain an orientation of the rivet relative to the tip;

without removing the rivet from the tip of the tool and thereby maintaining an orientation of the shank relative to the tip:
  removing the rivet from the die,
  transferring the rivet from the die to the scaffold using the tool, and
  placing the shank through a hole of the scaffold,
  wherein the rivet head rests on one of a luminal and abluminal surface of the strut and a tail of the shank extends out from the other of the luminal and abluminal surface; and
forming an interference fit between the rivet and hole including deforming the tail.

14. The method of claim 13, wherein the die comprises a plate having a hole and a counter bore.

15. The method of claim 13, wherein a push-out force for the shank from the hole is about an 80 gram-force.

16. The method of claim 13, wherein the scaffold has a strut thickness and a shank of the rivet has a length that is between 125% and 150% of the strut thickness.

17. The method of claim 13, wherein before forming the interference fit the hole is a cylindrical hole and after forming the interference fit the hole is a tapered hole.

18. The method of claim 17, wherein the shank formed from the die is cylindrical, and the forming an interference fit includes deforming the shank into a frustum.

19. The method of claim 13, wherein the hole is a polygonal hole or an elliptical hole.

20. A method for making a medical device, comprising:
  using a polymer scaffold including a strut having a hole formed in the strut, wherein the strut has a thickness of between 80 and 120 microns measured between a first side of the strut and a second side of the strut and the strut comprises poly(L-lactide); and
  using a radiopaque rivet marker having a head and a shank; and
  placing the rivet into the hole so that the head is disposed on a first side of the strut; and
  swaging the rivet including making a deformed shank from the shank while the rivet sits in the hole;
  wherein before swaging the hole is cylindrical and after swaging the hole is tapered, and
  wherein before swaging the shank is cylindrical and after swaging the shank forms a frustum.

21. The method of claim 20, wherein the shank has a tail extending beyond a second side of the strut and outside the hole before swaging, and after swaging the tail is substantially within the hole.

* * * * *